(12) United States Patent
Hatakeyama et al.

(10) Patent No.: US 11,517,236 B2
(45) Date of Patent: Dec. 6, 2022

(54) BIO-ELECTRODE COMPOSITION, BIO-ELECTRODE, AND METHOD FOR MANUFACTURING A BIO-ELECTRODE

(71) Applicant: SHIN-ETSU CHEMICAL CO., LTD., Tokyo (JP)

(72) Inventors: Jun Hatakeyama, Joetsu (JP); Motoaki Iwabuchi, Joetsu (JP); Yasuyoshi Kuroda, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 832 days.

(21) Appl. No.: 16/454,766

(22) Filed: Jun. 27, 2019

(65) Prior Publication Data

US 2020/0015699 A1 Jan. 16, 2020

(30) Foreign Application Priority Data

Jul. 12, 2018 (JP) .............................. JP2018-132116

(51) Int. Cl.
 *A61B 5/25* (2021.01)
 *A61B 5/259* (2021.01)
 (Continued)

(52) U.S. Cl.
 CPC ............ *A61B 5/259* (2021.01); *C08G 77/045* (2013.01); *C08K 3/041* (2017.05); *C08K 3/08* (2013.01);
 (Continued)

(58) Field of Classification Search
 CPC ..... A61B 5/25; A61B 5/259; A61B 2561/125; C07F 7/1804; C08K 3/04; C08K 3/041;
 (Continued)

(56) References Cited

U.S. PATENT DOCUMENTS

| 5,981,680 A | 11/1999 | Petroff et al. |
| 8,507,290 B2 * | 8/2013 | Liu ........................... C07F 7/21 436/63 |

(Continued)

FOREIGN PATENT DOCUMENTS

| CN | 102633953 A | * | 8/2012 |
| CN | 103570885 A | * | 2/2014 |

(Continued)

OTHER PUBLICATIONS

Long, Lizhen et al., "Polymer Electrolytes for Lithium Polymer Batteries", Journal of Materials Chemistry A, vol. 4, pp. 10038-10069, (2016).

(Continued)

*Primary Examiner* — Sanza L. McClendon
(74) *Attorney, Agent, or Firm* — Oliff PLC

(57) ABSTRACT

The present invention provides a bio-electrode composition including a silsesquioxane bonded to an N-carbonyl sulfonamide salt, wherein the N-carbonyl sulfonamide salt is shown by the following general formula (1):

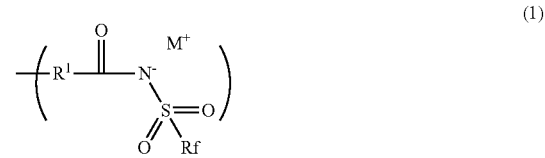

wherein $R^1$ represents a linear, branched, or cyclic alkylene group having 1 to 20 carbon atoms that may have an aromatic group, an ether group, or an ester group, or an arylene group having 6 to 10 carbon atoms; Rf represents a linear, branched, or cyclic alkyl group having 1 to 4 carbon (Continued)

atoms containing at least one fluorine atom; $M^+$ is an ion selected from a lithium ion, a sodium ion, a potassium ion, and a silver ion. This can form a living body contact layer for a bio-electrode that is excellent in electric conductivity and biocompatibility, light-weight, manufacturable at low cost, and free from large lowering of the electric conductivity even though it is wetted with water or dried.

20 Claims, 2 Drawing Sheets

(51) Int. Cl.
*C08K 3/04* (2006.01)
*C08G 77/04* (2006.01)
*C08K 3/08* (2006.01)
*C09J 9/02* (2006.01)
*C09J 133/10* (2006.01)
*C09J 175/04* (2006.01)
*C09J 183/04* (2006.01)

(52) U.S. Cl.
CPC ............... *C09J 9/02* (2013.01); *C09J 133/10* (2013.01); *C09J 175/04* (2013.01); *C09J 183/04* (2013.01); *A61B 2562/125* (2013.01)

(58) Field of Classification Search
CPC .......... C08K 3/08; C08K 5/548; C08G 77/12; C08G 77/24; C08G 77/26; C08G 77/28; C08L 83/04; C09J 9/09; C09J 133/10; C09J 175/04; C09J 183/04; H01B 1/22; H01B 1/12; H01B 1/24; H01B 5/14
See application file for complete search history.

(56) References Cited

U.S. PATENT DOCUMENTS

| | | | | |
|---|---|---|---|---|
| 10,584,221 | B2 * | 3/2020 | Hatakeyama | ...... C08G 18/8116 |
| 11,193,003 | B2 * | 12/2021 | Hatakeyama | .......... C08G 77/20 |
| 2002/0177039 | A1 | 11/2002 | Lu et al. | |
| 2002/0188069 | A1 | 12/2002 | Sugo et al. | |
| 2008/0118860 | A1 | 5/2008 | Harada et al. | |
| 2009/0061358 | A1 | 3/2009 | Ohashi et al. | |
| 2010/0285407 | A1 | 11/2010 | Ogihara et al. | |
| 2015/0275060 | A1 | 10/2015 | Kuroda et al. | |
| 2016/0155530 | A1 | 6/2016 | Someya et al. | |
| 2017/0275510 | A1 | 9/2017 | Quan et al. | |
| 2018/0226679 | A1 * | 8/2018 | Pan | ....................... H01M 4/364 |
| 2019/0151648 | A1 * | 5/2019 | Hatakeyama | ........ C08G 18/718 |

FOREIGN PATENT DOCUMENTS

| | | | | | |
|---|---|---|---|---|---|
| CN | | 104045778 | A * | 9/2014 | |
| CN | | 104744650 | A * | 7/2015 | |
| JP | | H05-095924 | A | 4/1993 | |
| JP | | 2002-298913 | A | 10/2002 | |
| JP | | 2002-332305 | A | 11/2002 | |
| JP | | 2003-225217 | A | 8/2003 | |
| JP | | 2003-257487 | A | 9/2003 | |
| JP | | 2004-033468 | A | 2/2004 | |
| JP | | 2004-527902 | A | 9/2004 | |
| JP | | 2005-320418 | A | 11/2005 | |
| JP | | 2008-111103 | A | 5/2008 | |
| JP | | 2009-080474 | A | 4/2009 | |
| JP | | 2010-262230 | A | 11/2010 | |
| JP | | 2011-079946 | A | 4/2011 | |
| JP | | 2015-019806 | A | 2/2015 | |
| JP | | 2015-100673 | A | 6/2015 | |
| JP | | 2015-193803 | A | 11/2015 | |
| JP | | 2016-011338 | A | 1/2016 | |
| JP | | 2016-065238 | A | 4/2016 | |
| WO | WO-2011040882 | A2 * | 4/2011 | ............. B82Y 15/00 |
| WO | | 2013/039151 | A1 | 3/2013 | |
| WO | WO-2019045331 | A1 * | 3/2019 | ............... A61B 5/00 |
| WO | WO-2021060620 | A1 * | 4/2021 | ........... C09D 201/00 |

OTHER PUBLICATIONS

Snyder, J. F., et al., "Ion Conductivity of Comb Polysiloxane Polyelectrolytes Containing Oligoether and Perfluoroether Sidechains", Journal of the Electrochemical Society, vol. 150, No. 8, pp. A1090-A1094, (2003).

Nov. 22, 2019 Extended European Search Report issued in European Patent Application No. 19185109.6.

Jul. 6, 2021 Office Action issued in Japanese Patent Application No. 2018-132116.

* cited by examiner

[FIG. 1]
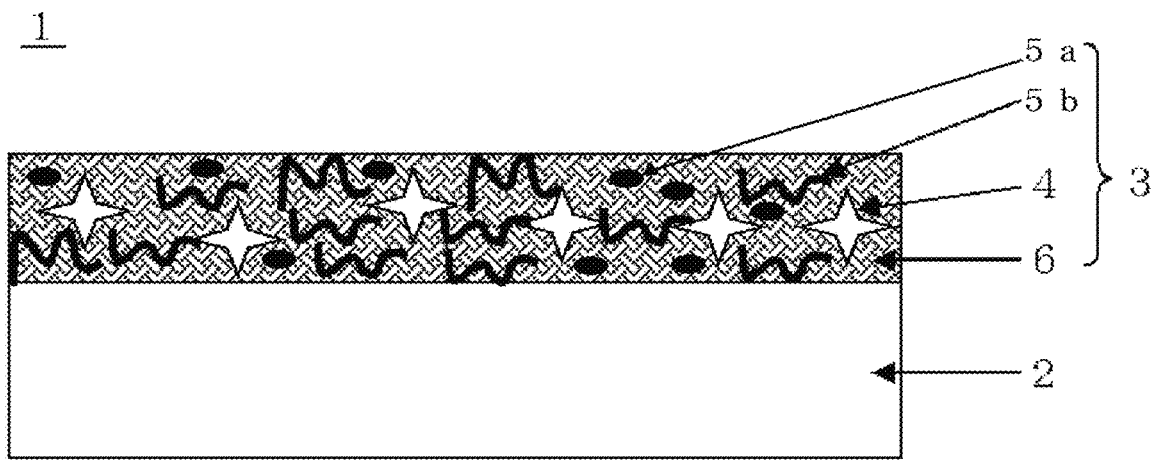
[FIG. 2]
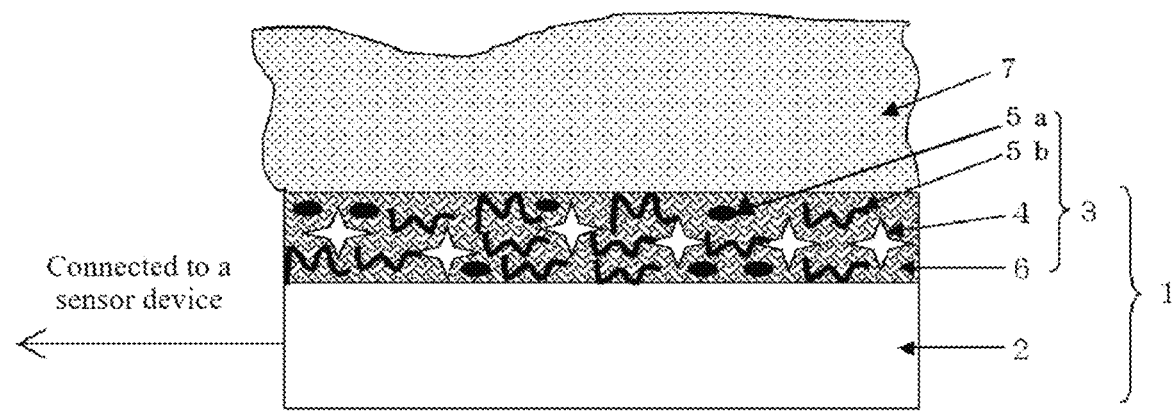
[FIG. 3A]
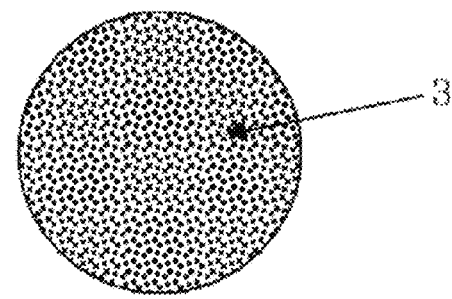

[FIG. 3B]
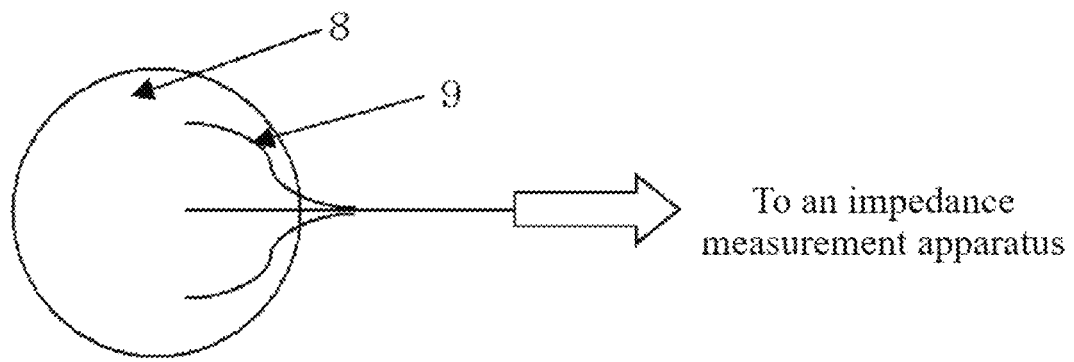
[FIG. 4]
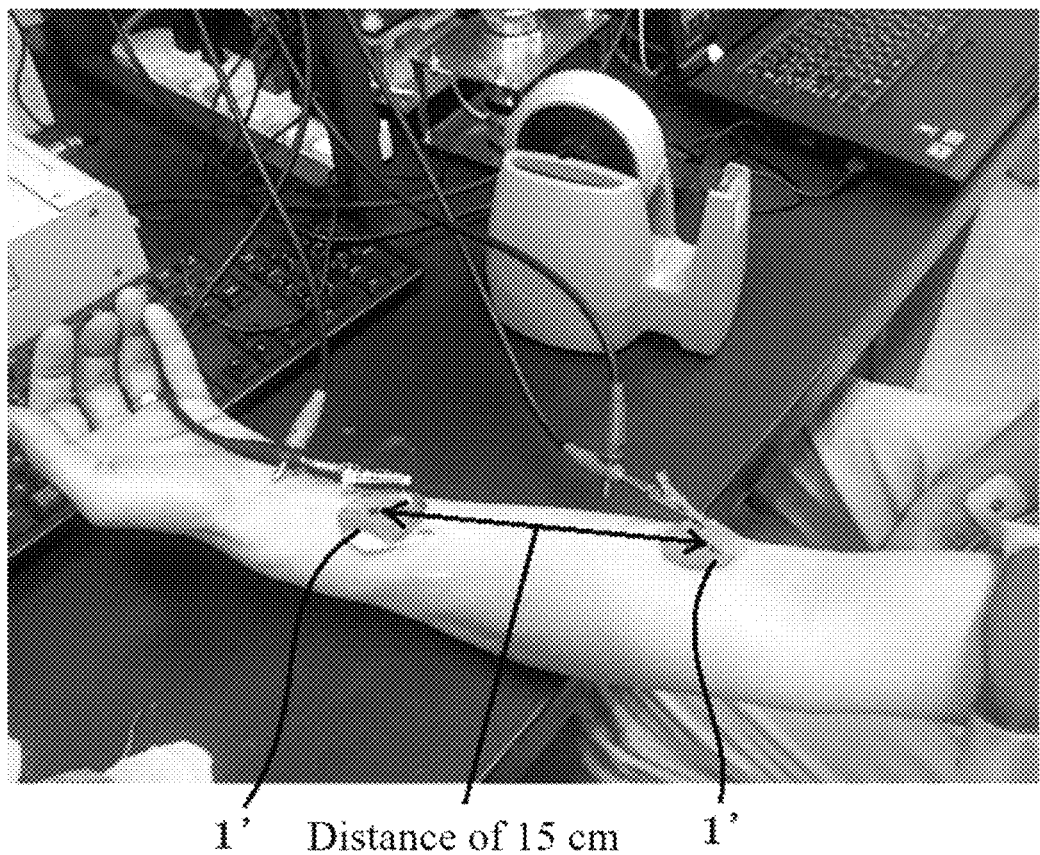

BIO-ELECTRODE COMPOSITION, BIO-ELECTRODE, AND METHOD FOR MANUFACTURING A BIO-ELECTRODE

TECHNICAL FIELD

The present invention relates to a bio-electrode that is used in contact with the skin of a living body capable of detecting physical conditions such as heart rate by an electric signal transmitted from the skin, a method for manufacturing the bio-electrode, and a bio-electrode composition desirably used for a bio-electrode.

BACKGROUND ART

A recent growing popularity of Internet of Things (IoT) has accelerated the development of such major wearable devices as watches and glasses that allow for Internet access. Even in the fields of medicine and sports, wearable devices for constantly monitoring the user's physical state are increasingly demanded, and such technological development is expected to be further encouraged.

In the field of medicine, including an electrocardiogram for detecting an electric signal to measure the motion of the heart, use of wearable devices for monitoring the state of human organs by detecting extremely weak current has been examined. The electrocardiogram measurement is conducted by attaching an electrode coated with an electro-conductive paste to a body, but this is a single (not continuous), short-time measurement. On the other hand, the above medical wearable device is aimed at constantly monitoring the state of physical conditions for a few weeks. Accordingly, a bio-electrode used in a medical wearable device is required to make no changes in electric conductivity even in long-time use and cause no skin allergy. In addition to these, bio-electrodes must be light-weight and produced at low cost.

Medical wearable devices are classified into two types: direct body attachment and clothing attachment. One typical body attachment device is a bio-electrode formed of a hydrophilic gel containing water and electrolytes as ingredients of the above electro-conductive paste (Patent Document 1). The hydrophilic gel, containing sodium, potassium, and calcium electrolytes in a hydrophilic polymer containing water, detects changes in ion concentration from the skin to convert the data into electricity. Meanwhile, one typical clothing attachment device is characterized by a method for using as an electrode a fabric including an electro-conductive polymer, such as PEDOT-PSS (Poly-3,4-ethylenedioxy-thiophene-polystyrenesulfonate), and a silver paste incorporated into the fiber (Patent Document 2).

However, the use of the hydrophilic gel containing water and electrolytes unfortunately brings about loss of electric conductivity due to water evaporation in drying process. Meanwhile, the use of a higher ionization tendency metal such as copper can cause some users to suffer from skin allergy. The use of an electro-conductive polymer such as PEDOT-PSS can also cause skin allergy due to the strong acidity of the electro-conductive polymer, as well as peeling of the electro-conductive polymer from fibers during washing.

By taking advantage of excellent electric conductivity, the use of electrode materials formed of metal nanowire, carbon black, or carbon nanotube has been examined (Patent Document 3, 4, and 5). With higher contact probability, metal nanowires can conduct electricity in small quantities to be added. Nevertheless, metal nanowires, formed of a pointed thin material, may cause skin allergy. Accordingly, even though these electrode materials themselves cause no allergic reaction, the biocompatibility can be degraded depending on the shape of a material and its inherent stimulation, thereby failing to satisfy both electric conductivity and biocompatibility.

Although metal films seem to function as an excellent bio-electrode thanks to extremely high electric conductivity, this is not always the case. Upon heartbeat, the human skin releases a sodium ion, a potassium ion, or a calcium ion, instead of extremely weak current. It is thus necessary to convert changes in ion concentration into current, which is what less ionized precious metals unfortunately fail to do efficiently. The resulting bio-electrode including the precious metal is characterized by high impedance and high resistance to the skin during electrical conduction.

Meanwhile, the use of a battery containing an ionic liquid has been examined (Patent Document 6). Advantageously, the ionic liquid is thermally and chemically stable, and the electric conductivity is excellent, providing more various battery applications. However, an ionic liquid having smaller molecular weight shown in Patent Document 6 unfortunately dissolves into water. A bio-electrode containing such an ionic liquid in use allows the ionic liquid to be extracted from the electrode by sweating, which not only lowers the electric conductivity, but also causes rough skin by the liquid soaking into the skin.

Batteries using a lithium salt of polymer type sulfonimide have been investigated (Non-Patent Document 1). Lithium has been applied to batteries because of their high ionic mobility, however, this is not a material with bio-compatibility. Additionally, lithium salts of fluorosulfonate have been investigated in a form of a pendant on silicone (Non-Patent Document 2).

The bio-electrode fails to give biological information when it is apart from the skin. The detection of even changes in contact area can vary quantities of electricity traveling through the electrode, allowing the baseline of an electrocardiogram (electric signal) to fluctuate. Accordingly, in order to stably detect electric signals from the body, the bio-electrode is required to be in constant contact with the skin and make no changes in contact area. This requirement is satisfied, preferably by use of adhesive biomedical electrodes. Moreover, elastic and flexible biomedical electrodes are needed to follow changes in skin expansion and flexion.

CITATION LIST

Patent Literature

Patent Document 1: International Patent Laid-Open Publication No. WO 2013/039151
Patent Document 2: Japanese Unexamined Patent Application Publication No. 2015-100673
Patent Document 3: Japanese Unexamined Patent Application Publication No. H5-095924
Patent Document 4: Japanese Unexamined Patent Application Publication No. 2003-225217
Patent Document 5: Japanese Unexamined Patent Application Publication No. 2015-019806
Patent Document 6: Japanese Unexamined Patent Application Publication No. 2004-527902

Non Patent Literature

Non Patent Document 1: J. Mater. Chem. A, 2016, 4, p 10038-10069
Non Patent Document 2: J. of the Electrochemical Society, 150(8), A1090-A1094 (2003)

SUMMARY OF INVENTION

Technical Problem

The present invention was made in view of the situation to solve the problems, and has an object to provide a bio-electrode composition capable of forming a living body contact layer for a bio-electrode that is excellent in electric conductivity and biocompatibility, is light-weight, can be manufactured at low cost, and can control significant reduction in electric conductivity even though the bio-electrode is wetted with water or dried, a bio-electrode including a living body contact layer formed of the bio-electrode composition, and a method for manufacturing the bio-electrode.

Solution to Problem

To solve the above problems, the present invention provides a bio-electrode composition comprising a silsesquioxane bonded to an N-carbonyl sulfonamide salt, wherein the N-carbonyl sulfonamide salt is shown by the following general formula (1):

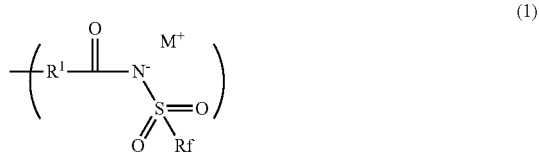

(1)

wherein $R^1$ represents a linear, branched, or cyclic alkylene group having 1 to 20 carbon atoms or an arylene group having 6 to 10 carbon atoms, with the alkylene group optionally having an aromatic group, an ether group, or an ester group; Rf represents a linear, branched, or cyclic alkyl group having 1 to 4 carbon atoms and containing at least one fluorine atom; $M^+$ is an ion selected from a lithium ion, a sodium ion, a potassium ion, and a silver ion.

The bio-electrode composition like this is capable of forming a living body contact layer for a bio-electrode that is excellent in electric conductivity and biocompatibility, light-weight, manufacturable at low cost, and free from large lowering of the electric conductivity even though it is wetted with water or dried.

It is preferable that the silsesquioxane bonded to an N-carbonyl sulfonamide salt have a repeating unit-a shown by the following general formula (2):

(2)

wherein $R^1$, Rf, and $M^+$ are as defined above.

With the repeating unit-a like this, the bio-electrode composition is allowed to form a living body contact layer for a bio-electrode that is particularly excellent in electric conductivity and biocompatibility, light-weight, manufacturable at low cost, and free from large lowering of the electric conductivity even though it is wetted with water or dried.

It is preferable that the inventive bio-electrode composition further comprise an adhesive resin as a component (B) in addition to the silsesquioxane bonded to an N-carbonyl sulfonamide salt as a component (A).

With both of the component (A) and the component (B) described above, the component (B) compatibilizes the component (A) to prevent elution of the salt, and the composition is allowed to improve the adhesion.

In this case, it is preferable that the component (B) be one or more resins selected from a silicone resin, a (meth) acrylate resin, and a urethane resin.

With the component (B) like this, the bio-electrode composition is more securely prevented from elution of the component (A) and can be improved in adhesion.

It is preferable that the component (B) contain diorganosiloxane having an alkenyl group, and organohydrogenpolysiloxane having an SiH group.

With the component (B) like this, the bio-electrode composition is still more securely prevented from elution of the component (A) and can be further improved in adhesion.

In this case, it is preferable that the component (B) further contain a silicone resin having an $R_xSiO_{(4-x)/2}$ unit (wherein, R represents a substituted or unsubstituted monovalent hydrocarbon group having 1 to 10 carbon atoms, and "x" is a number in a range of 2.5 to 3.5) and an $SiO_2$ unit.

This allows the bio-electrode composition to be still more securely prevented from elution of the component (A) and can be further improved in adhesion.

It is preferable that the inventive bio-electrode composition further comprise a carbon powder and/or a metal powder as a component (C).

This makes the cured material of the bio-electrode composition excellent in electric conductivity.

It is preferable that the carbon powder as the component (C) be either or both of carbon black and carbon nanotube.

This makes the bio-electrode composition particularly excellent in electric conductivity.

It is preferable that the metal powder as the component (C) be a powder of a metal selected from gold, silver, platinum, copper, tin, titanium, nickel, aluminum, tungsten, molybdenum, ruthenium, chromium, and indium. It is more preferable that the metal powder be a silver powder.

The component (C) like this makes it possible to further improve the electronic conductivity of the inventive bio-electrode composition. Particularly, a silver powder is excellent in view of electric conductivity, cost, and biocompatibility.

It is preferable that the bio-electrode composition further comprise an organic solvent as a component (D).

The bio-electrode composition like this is further improved in the coating properties.

The present invention also provides a bio-electrode comprising an electro-conductive base material and a living body contact layer formed on the electro-conductive base material;

wherein the living body contact layer is a cured material of the bio-electrode composition described above.

With the silsesquioxane bonded to an N-carbonyl sulfonamide salt (N-carbonyl sulfonamide salt-silsesquioxane), the inventive bio-electrode is allowed to achieve both of electric conductivity and biocompatibility, and is also allowed to have adhesion, thereby making it possible to keep the contact area with skin constant to obtain electric signals from skin stably with high sensitivity.

It is preferable that the electro-conductive base material comprise one or more species selected from gold, silver, silver chloride, platinum, aluminum, magnesium, tin, tungsten, iron, copper, nickel, stainless steel, chromium, titanium, carbon, and an electro-conductive polymer.

In the bio-electrode of the present invention, these electro-conductive base materials can be used particularly favorably.

The present invention also provides a method for manufacturing a bio-electrode having an electro-conductive base material and a living body contact layer formed on the electro-conductive base material, comprising:

applying the bio-electrode composition described above onto the electro-conductive base material; and curing the bio-electrode composition; thereby forming the living body contact layer.

The inventive method for manufacturing a bio-electrode makes it possible to manufacture the inventive bio-electrode, which is excellent in electric conductivity and biocompatibility, light-weight, and free from large lowering of the electric conductivity even though it is wetted with water or dried, easily and at low cost.

It is preferable that the electro-conductive base material comprise one or more species selected from gold, silver, silver chloride, platinum, aluminum, magnesium, tin, tungsten, iron, copper, nickel, stainless steel, chromium, titanium, carbon, and an electro-conductive polymer.

In the inventive method for manufacturing a bio-electrode, these electro-conductive base materials can be used particularly favorably.

The present invention also provides an alkoxysilane compound shown by the following general formula (3):

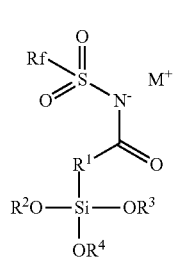

(3)

wherein $R^1$ represents a linear, branched, or cyclic alkylene group having 1 to 20 carbon atoms or an arylene group having 6 to 10 carbon atoms, with the alkylene group optionally having an aromatic group, an ether group, or an ester group; $R^2$ to $R^4$ each represent a hydrogen atom or a linear or branched alkyl group having 1 to 4 carbon atoms; Rf represents a linear, branched, or cyclic alkyl group having 1 to 4 carbon atoms and containing at least one fluorine atom; $M^+$ is an ion selected from a lithium ion, a sodium ion, a potassium ion, and a silver ion.

The alkoxysilane compound like this is useful as a precursor for synthesizing the silsesquioxane bonded to an N-carbonyl sulfonamide salt to constitute the inventive bio-electrode composition.

The present invention also provides a silsesquioxane comprising a repeating unit shown by the following general formula (2), and having a weight average molecular weight in a range of 600 to 1000000,

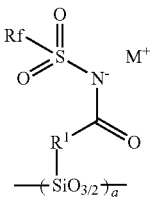

(2)

wherein $R^1$ represents a linear, branched, or cyclic alkylene group having 1 to 20 carbon atoms or an arylene group having 6 to 10 carbon atoms, with the alkylene group optionally having an aromatic group, an ether group, or an ester group; Rf represents a linear, branched, or cyclic alkyl group having 1 to 4 carbon atoms and containing at least one fluorine atom; $M^+$ is an ion selected from a lithium ion, a sodium ion, a potassium ion, and a silver ion.

The silsesquioxane like this is particularly useful as the component of a bio-electrode composition to form a living body contact layer for a bio-electrode that is capable of conducting electric signals from skin efficiently to a device (i.e., excellent in electric conductivity), free from the risk of causing allergies even when it is worn on skin for a long time (i.e., excellent in biocompatibility), and free from large lowering of the electric conductivity even though it is wetted with water or dried.

Advantageous Effects of Invention

As described above, the inventive bio-electrode composition makes it possible to form a living body contact layer for a bio-electrode that is capable of conducting electric signals from skin efficiently to a device (i.e., excellent in electric conductivity), free from the risk of causing allergies even when it is worn on skin for a long time (i.e., excellent in biocompatibility), light-weight, manufacturable at low cost, and free from large lowering of the electric conductivity even though it is wetted with water or dried. The electric conductivity can be further improved by adding an electro-conductive powder (carbon powder, metal powder), and a bio-electrode can be produced with particularly high adhesion and stretchability by combination of a resin that has adhesion and stretchability. Additionally, the stretchability and the adhesion to skin can be improved using additives and can be controlled by adjusting the composition of resin or the thickness of living body contact layer.

With the sulfonamide salt-silsesquioxane described above, the inventive bio-electrode is allowed to achieve both of electric conductivity and biocompatibility, and is also allowed to have adhesion, thereby making it possible to keep the contact area with skin constant to obtain electric signals from skin stably with high sensitivity.

Additionally, the inventive method for manufacturing a bio-electrode makes it possible to manufacture the inventive bio-electrode, which is excellent in electric conductivity and biocompatibility, light-weight, and free from large lowering of the electric conductivity even though it is wetted with water or dried, easily at low cost.

BRIEF DESCRIPTION OF DRAWINGS

FIG. 1 is a schematic sectional view showing an example of a bio-electrode of the present invention;

FIG. 2 is a schematic sectional view showing an example of the inventive bio-electrode worn on a living body;

FIG. 3A is a schematic view of the bio-electrode produced in Examples of the present invention viewed from the living body contact layer side;

FIG. 3B is a schematic view of the bio-electrode produced in Examples of the present invention viewed from the electro-conductive base material side; and FIG. 4 is a photograph of a scene of measuring impedance on the surface of skin by using the bio-electrode produced in Examples of the present invention.

DESCRIPTION OF EMBODIMENTS

As described above, it has been desired to develop a bio-electrode composition capable of forming a living body contact layer for a bio-electrode that is excellent in electric conductivity and biocompatibility, light-weight, manufacturable at low cost, and free from large lowering of the electric conductivity even though it is wetted with water or dried; a bio-electrode in which the living body contact layer is formed from the bio-electrode composition; and a method for manufacturing the same.

The surface of skin releases ions of sodium, potassium, and calcium in accordance with heartbeat. The bio-electrode have to convert the increase and decrease of these ions released from skin to electric signals. Accordingly, the bio-electrode have to be composed of a material that is excellent in ionic conductivity to transmit the increase and decrease of ions.

The present inventors have noticed ionic liquids as a material that is highly ionic conductive. Ionic liquids are characterized by high thermal and chemical stability as well as excellent electric conductivity, thereby having been widely used for battery uses. Illustrative examples of known ionic liquid include hydrochloric acid salt, hydrobromic acid salt, hydroiodic acid salt, trifluoromethanesulfonic acid salt, nonafluorobutanesulfonic acid salt, bis(trifluoromethanesulfonyl)imide acid salt, hexafluorophosphate salt, and tetrafluoroborate salt of sulfonium, phosphonium, ammonium, morpholinium, pyridinium, pyrrolidinium, and imidazolium. However, these salts (particularly, the ones with low molecular weight) are generally liable to hydrate, thereby causing a defect such that the salt is extracted with perspiration or by washing to lower the electric conductivity of a bio-electrode in which the living body contact layer is formed from a bio-electrode composition containing these salts. In addition, the tetrafluoroborate salt is highly toxic, and the other salts are highly water-soluble to easily permeate into skin, thereby causing an issue of rough dry skin (i.e., highly irritative to skin).

In neutralized salts formed from highly acidic acids, the ions are strongly polarized to improve the ionic conductivity. This is the reason why lithium salts of bis(trifluoromethanesulfonyl)imidic acid and tris(trifluoromethanesulfonyl)methide acid show high ionic conductivity as a lithium ion battery. On the other hand, the higher acidity makes the salt have stronger irritation to a body. That is, ionic conductivity and irritation to a body are in relation of trade-off. In a salt applied to a bio-electrode, however, higher ionic conductivity and lower irritation to a body have to be combined.

The salt compound decreases the permeability and irritation to skin as the molecular weight is larger or the structure is of higher order in three dimensions. Accordingly, the salt compound bonded to silsesquioxane (SSQ) is ideal because of the large molecular weight and the three-dimensional structure. Thus the present inventors have conceived to synthesize a silsesquioxane compound bonded to a salt having an ionic sulfonamide group.

The present inventors have also conceived that the use of this salt mixed with adhesive (resin), such as a silicone type, an acrylic type, and a urethane type, makes it possible to achieve continuous adhesion to skin to obtain electric signals that are stable for a long time.

The inventors have diligently studied the above subjects and found that higher ionic conductivity alone is sometimes inadequate to form a bio-electrode with higher sensitivity, and higher electronic conductivity can also be necessary; the electronic conductivity is improved efficiently by adding particles of carbon or metal; this allows the bio-electrode to function as a highly sensitive bio-electrode with lower impedance; thereby bringing the present invention to completion.

That is, the present invention is a bio-electrode composition comprising a silsesquioxane bonded to an N-carbonyl sulfonamide salt, wherein the N-carbonyl sulfonamide salt is shown by the following general formula (1):

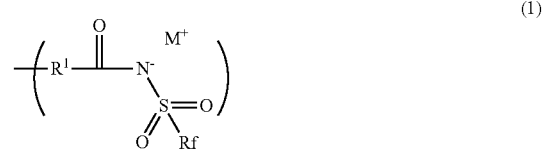

wherein $R^1$ represents a linear, branched, or cyclic alkylene group having 1 to 20 carbon atoms or an arylene group having 6 to 10 carbon atoms, with the alkylene group optionally having an aromatic group, an ether group, or an ester group; Rf represents a linear, branched, or cyclic alkyl group having 1 to 4 carbon atoms and containing at least one fluorine atom; $M^+$ is an ion selected from a lithium ion, a sodium ion, a potassium ion, and a silver ion.

Hereinafter, the present invention will be described specifically, but the present invention is not limited thereto.

<Bio-Electrode Composition>

It is essential that the inventive bio-electrode composition contains a silsesquioxane (SSQ) bonded to an N-carbonyl sulfonamide salt, and the N-carbonyl sulfonamide salt is shown by the general formula (1). The bio-electrode composition may also contain both of (A) the silsesquioxane compound bonded to an N-carbonyl sulfonamide salt and an adhesive resin. The bio-electrode composition can also contain an electro-conductive powder (carbon powder, metal powder) or an organic solvent additionally.

Hereinafter, each component will be described more specifically. Incidentally, the following describes the silsesquioxane bonded to an N-carbonyl sulfonamide salt as "a component (A)", an adhesive resin as "a component (B)", an electro-conductive powder as "a component (C)", and additives such as an organic solvent as "a component (D)" also.

[Component (A)]

The inventive bio-electrode composition contains a component (A) (a silsesquioxane bonded to an N-carbonyl sulfonamide salt) as (A) an ionic material (salt). The ionic material (salt) added to the bio-electrode composition as an electro-conductive material is a silsesquioxane compound bonded to a lithium salt, a sodium salt, a potassium salt, or a silver salt of an N-carbonyl sulfonamide shown by the general formula (1) described below. Incidentally, the silsesquioxane bonded to an N-carbonyl sulfonamide salt is also referred to as "an N-carbonyl sulfonamide salt-silsesquioxane" or "an N-carbonyl sulfonamide salt-SSQ" below.

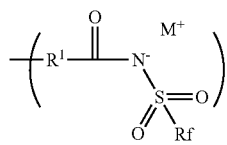
(1)

In the formula, R¹ represents a linear, branched, or cyclic alkylene group having 1 to 20 carbon atoms that may have an aromatic group, an ether group, or an ester group, or an arylene group having 6 to 10 carbon atoms; Rf represents a linear, branched, or cyclic alkyl group having 1 to 4 carbon atoms and containing at least one fluorine atom; M⁺ is an ion selected from a lithium ion, a sodium ion, a potassium ion, and a silver ion.

The N-carbonyl sulfonamide salt-silsesquioxane preferably has a repeating unit-a shown by the following general formula (2):

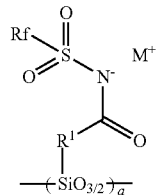
(2)

wherein R¹ represents a linear, branched, or cyclic alkylene group having 1 to 20 carbon atoms that may have an aromatic group, an ether group, or an ester group, or an arylene group having 6 to 10 carbon atoms; Rf represents a linear, branched, or cyclic alkyl group having 1 to 4 carbon atoms and containing at least one fluorine atom; M⁺ is an ion selected from a lithium ion, a sodium ion, a potassium ion, and a silver ion.

As the repeating unit-a shown by the general formula (2), the following ones can be exemplified specifically.

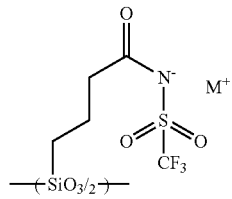
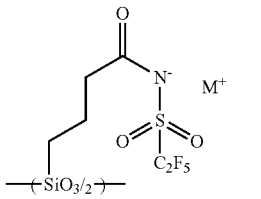
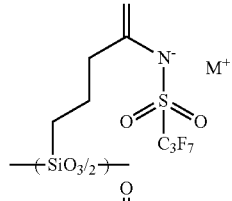
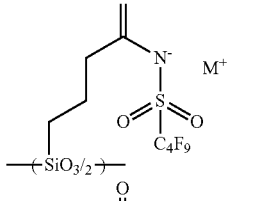
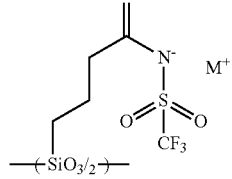
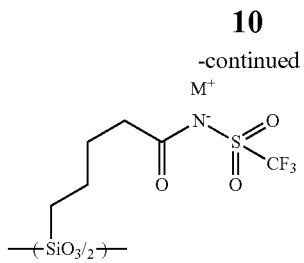
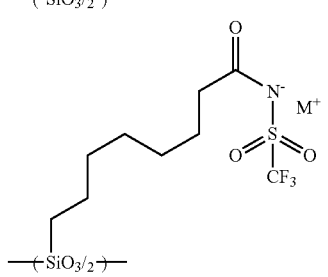
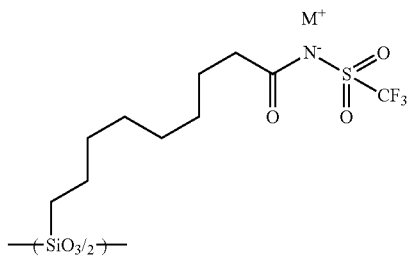
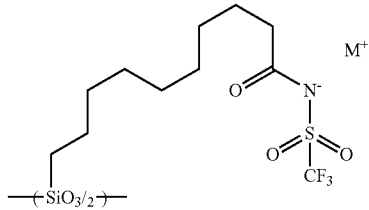
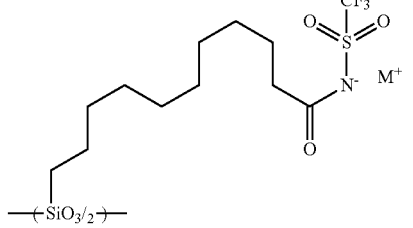

-continued
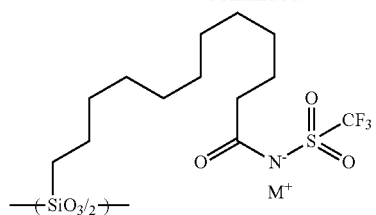
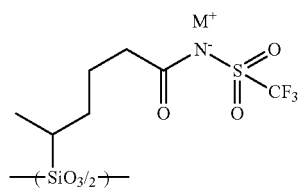
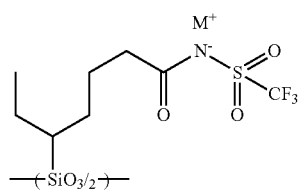
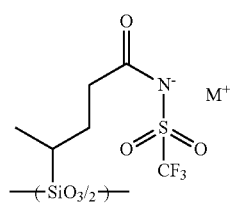
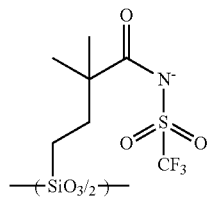
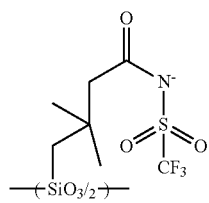
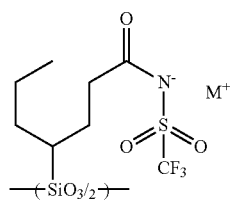
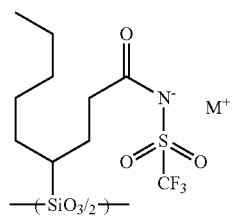
-continued
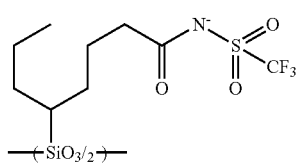
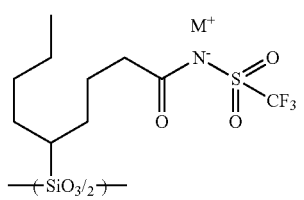
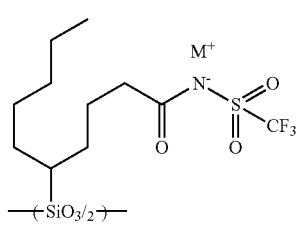
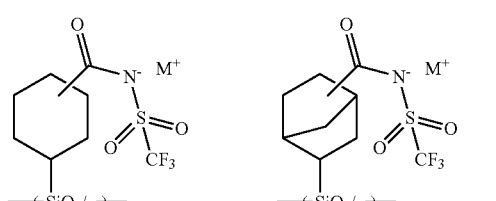
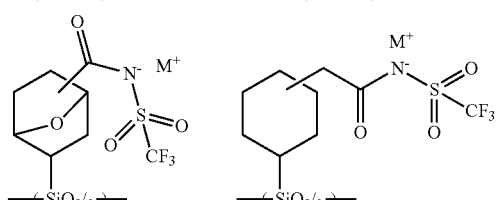
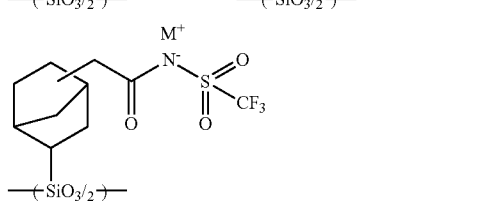
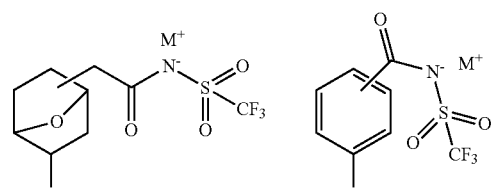
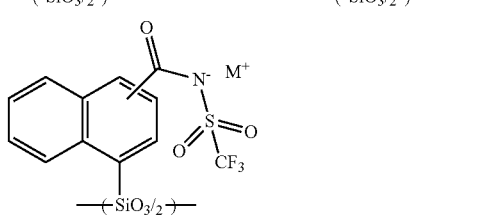

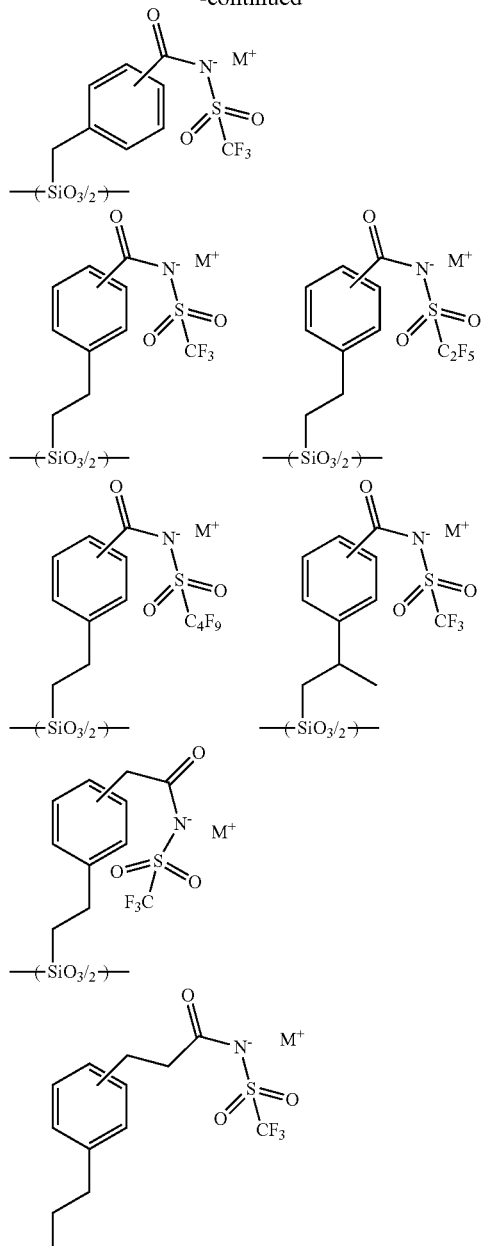
Hereinabove, M⁺ is as defined above.
(Repeating Unit-b)
The component (A) of the inventive bio-electrode composition may contain a repeating unit-b composed of silsesquioxane having a glyme chain in addition to the repeating unit-a in order to improve the electric conductivity. As the repeating unit-b, the following ones can be exemplified specifically.
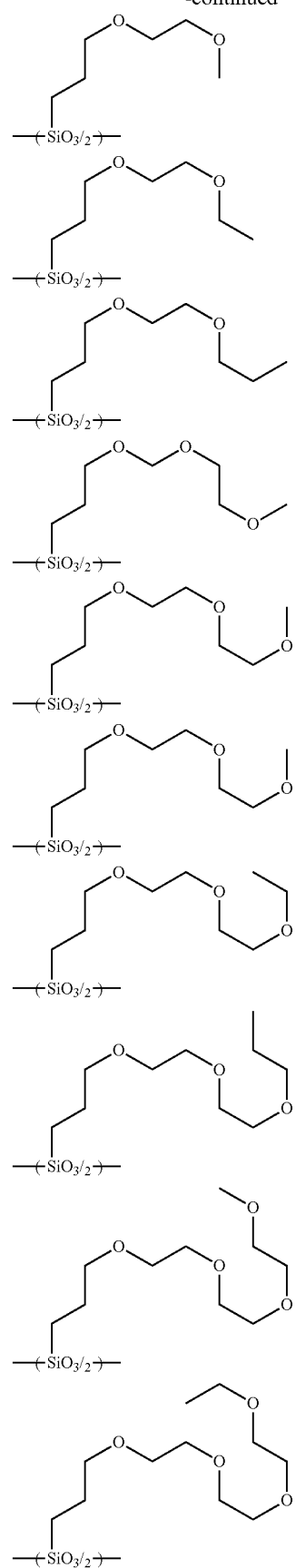

-continued
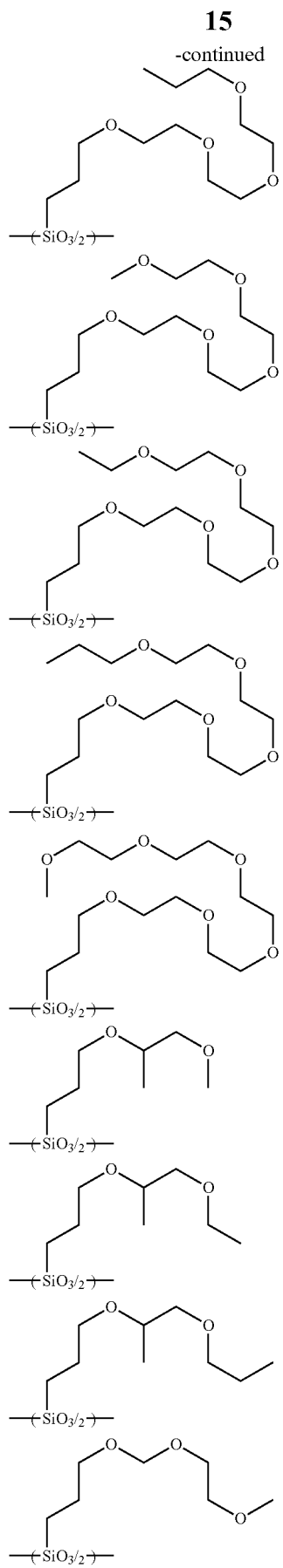
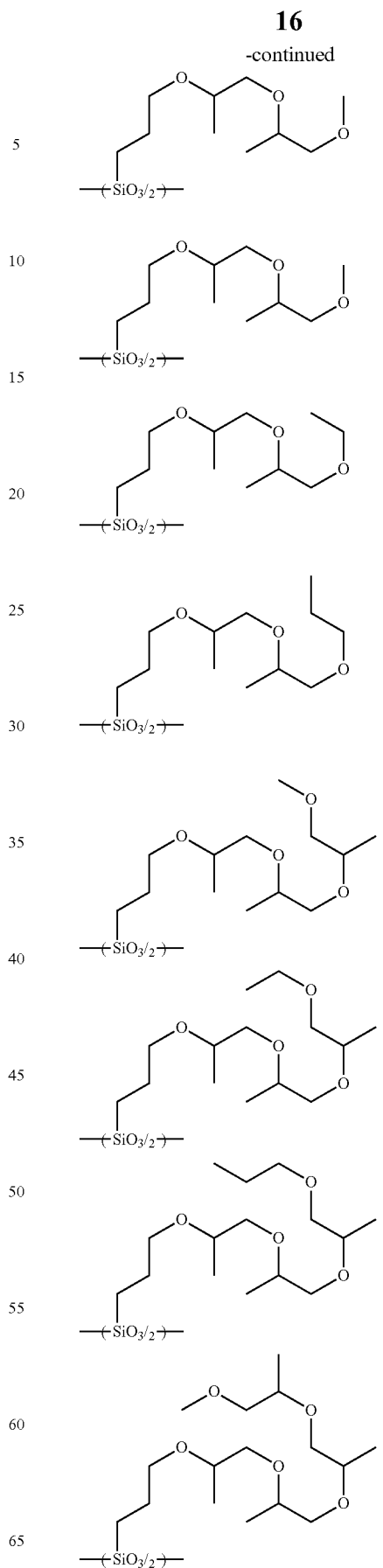

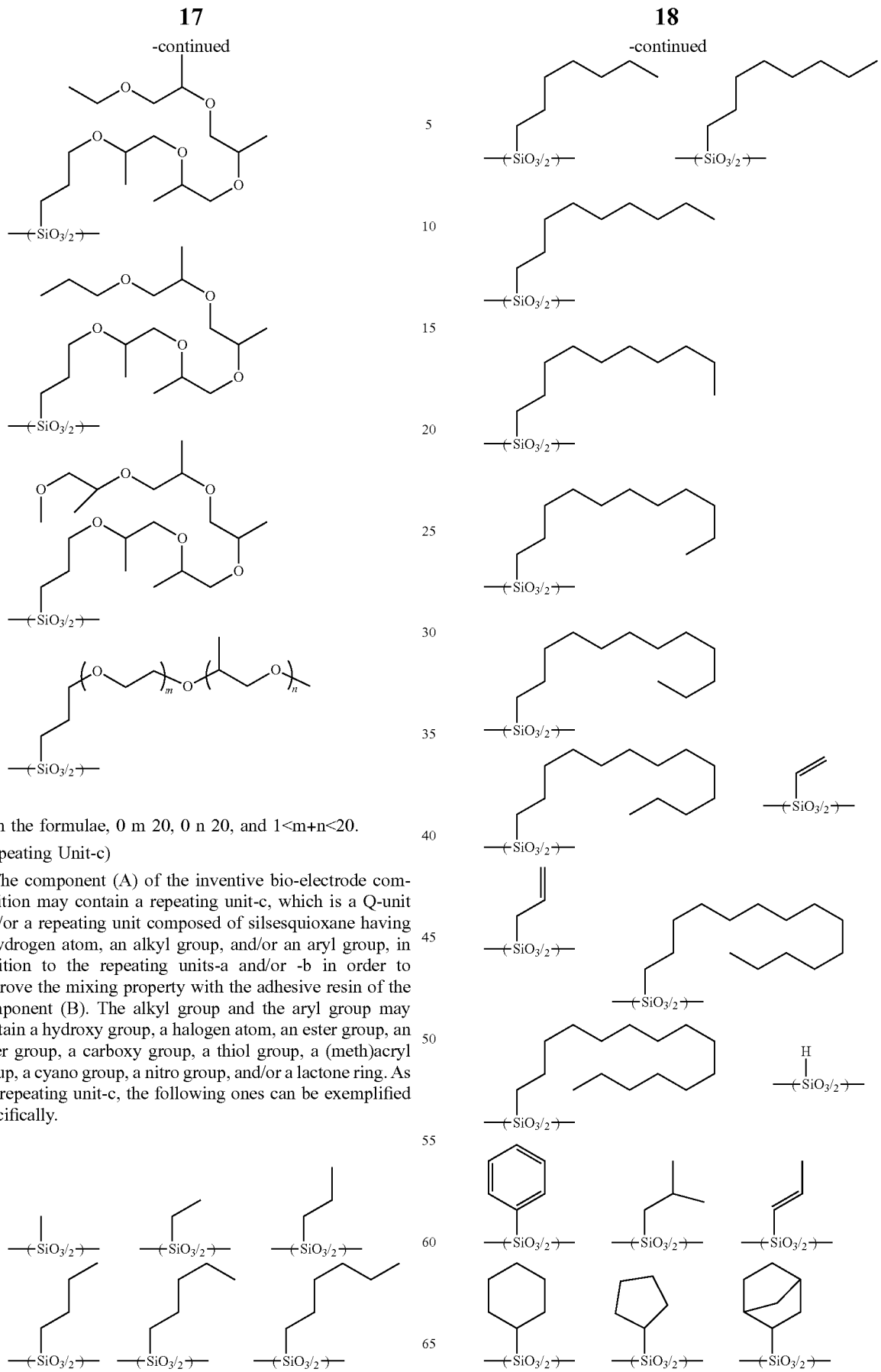

In the formulae, 0 m 20, 0 n 20, and 1<m+n<20.

(Repeating Unit-c)

The component (A) of the inventive bio-electrode composition may contain a repeating unit-c, which is a Q-unit and/or a repeating unit composed of silsesquioxane having a hydrogen atom, an alkyl group, and/or an aryl group, in addition to the repeating units-a and/or -b in order to improve the mixing property with the adhesive resin of the component (B). The alkyl group and the aryl group may contain a hydroxy group, a halogen atom, an ester group, an ether group, a carboxy group, a thiol group, a (meth)acryl group, a cyano group, a nitro group, and/or a lactone ring. As the repeating unit-c, the following ones can be exemplified specifically.

-continued
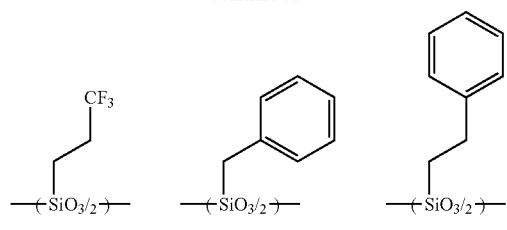
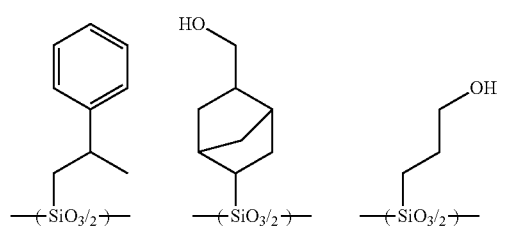
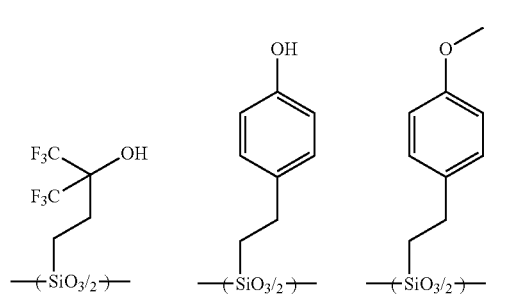
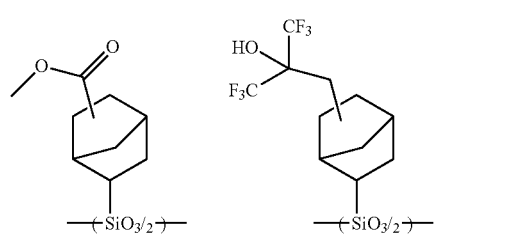
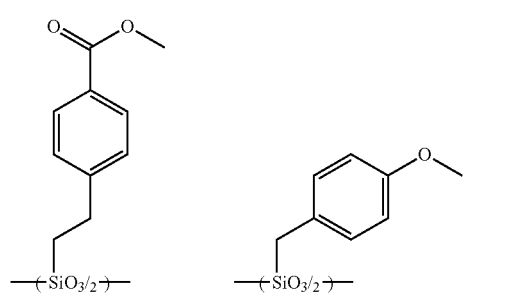
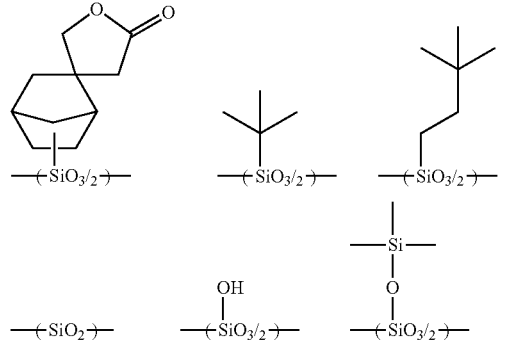
-continued
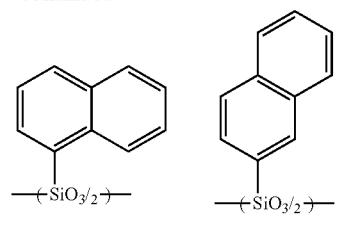
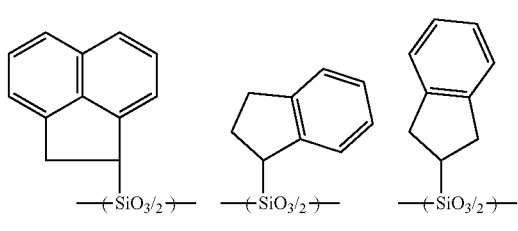
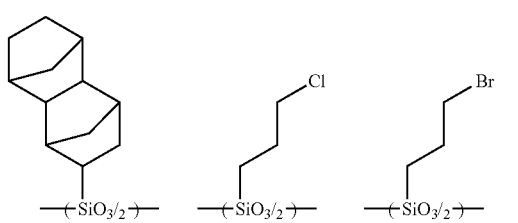
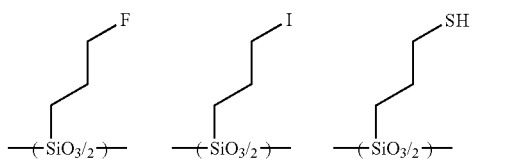
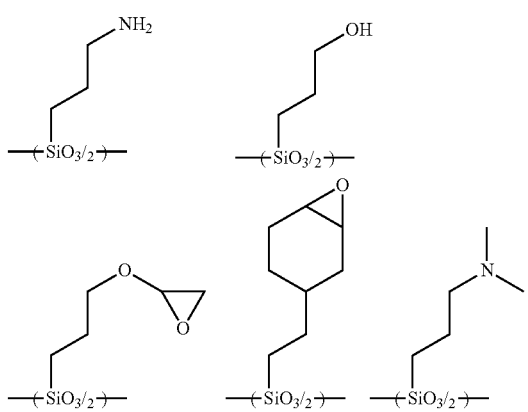
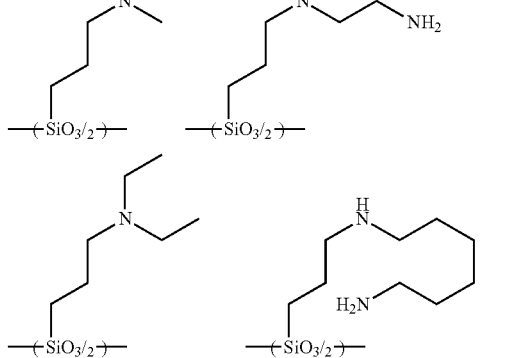

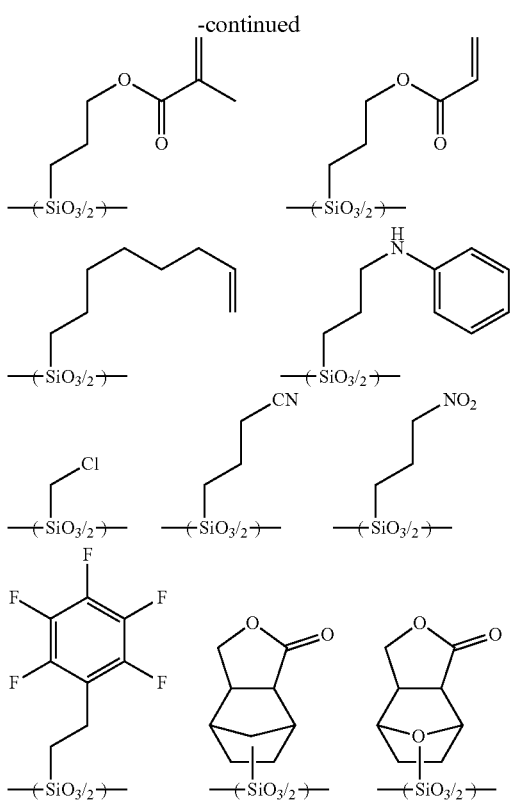

(Repeating Unit-d)

The component (A) of the inventive bio-electrode composition may have a repeating unit-d having a metal-oxygen bond in addition to the repeating units-a, -b, and/or -c described above by co-condensation of alkoxide of metal other than silicon. Illustrative examples of metal of the alkoxy metal other than silicon include boron, aluminum, gallium, yttrium, germanium, titanium, hafnium, tin, arsenic, antimony, niobium, tantalum, bismuth, phosphorus, vanadium, and zirconium. Alkoxy metals thereof are described in paragraphs 0061 to 0078 in JP 2010-262230A concretely.

As one of the method for synthesizing a polysilsesquioxane having the repeating unit-a (a-unit) of the component (A), a method by condensation reaction is exemplified using trialkoxysilane to be a precursor. The monomer to be this precursor can be obtained by hydrosilylation reaction of an N-carbonyl sulfonamide salt having a double bond and a trialkoxysilane compound having an Si—H group under a platinum catalyst.

Thus obtained compound can be shown by the following general formula (3):

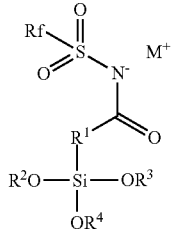 (3)

wherein $R^1$, Rf, and $M^+$ are as defined above; $R^2$ to $R^4$ each represent a hydrogen atom or a linear or branched alkyl group having 1 to 4 carbon atoms.

The repeating unit-b (b-unit) having a glyme chain can be obtained by hydrosilylation reaction of a compound having a double bond and an ether group, together with a trialkoxysilane compound having an Si—H group, under a platinum catalyst. The a-unit and the b-unit may be contained in the same polysilsesquioxane molecule or may be prepared by blending silsesquioxane compounds each having the a-unit or an ether group. The copolymerization ratio of units-a, -b, -c, and -d is such that $0<a<1.0$, $0\leq b<1.0$, $0\leq c<1.0$, and $0\leq d<1.0$; preferably $0.1\leq a<1.0$, $0\leq b\leq 0.9$, $0\leq c<0.9$, and $0\leq d<0.9$.

As the method for condensation of the trialkoxysilane, it is preferable to use a method described in paragraphs 0079 to 0099 in JP 2010-262230A, for example. Incidentally, the method can also be used in case of introducing the d-unit.

The polysilsesquioxane having the repeating unit-a (a-unit) of the component (A) can be synthesized by condensation reaction of the precursor (trialkoxysilane). Concretely, the polysilsesquioxane can be synthesized, for example, by mixing an N-carbonyl sulfonamide salt having a double bond, an ether compound having a double bond in accordance with needs, a trialkoxysilane compound having an SiH group, and a platinum catalyst, and heating to promote the hydrosilylation reaction to synthesize an N-carbonyl sulfonamide salt-trialkoxysilane compound (precursor), followed by condensation reaction of this precursor compound with another alkoxysilane(s) or alkoxide of metal(s) other than silicon in accordance with needs.

The polysilsesquioxane is desirably a polymer compound having a molecular weight of 600 or more and 1000000 or less. Having a pendant of the N-carbonyl sulfonamide salt on the polymeric silsesquioxane as described above, the salt compound comes to have a larger molecular weight and a higher order structure in three dimensions. In general, the salt compound decreases the permeability to skin to decrease irritation to skin as the molecular weight increases or the higher order structure (three-dimensional structure) develops. Accordingly, such a polymer compound can be more securely prevented from permeating to skin to cause allergies.

As described above, it is possible to synthesize a silsesquioxane having a repeating unit shown by the general formula (2) (N-carbonyl sulfonamide salt-SSQ) with a weight average molecular weight of 600 to 1000000. The silsesquioxane is suitable as an ionic material (salt) to be blended to the inventive bio-electrode composition as an electro-conductive material.

In the inventive bio-electrode composition, the amount of the component (A) is preferably 0.1 to 300 parts by mass, more preferably 1 to 200 parts by mass on the basis of 100 parts by mass of the component (B). The component (A) may be used singly or in admixture of two or more kinds.

[Component (B)]

The inventive bio-electrode composition can contain an adhesive resin as the component (B) in addition to the component (A). The component (B) contained in the bio-electrode composition is a component for compatibilizing (A) the ionic silsesquioxane material (N-carbonyl sulfonamide salt-SSQ) to prevent elution of the salt, for holding an electric conductivity improver such as carbon powders and/or metal powders, and for achieving adhesion; and is composed of an adherent resin. It is to be noted that the component (B) may be any of a resin other than the component (A) and is preferably either or both of a thermosetting resin and a photo-curable resin, particularly one or more resins selected from silicone resins (silicone base resins), (meth)acrylate resins (acrylic base resins), and urethane resins (urethane base resins).

The adherent silicone base resin include an addition-curable (addition reaction-curable) type and a radical curable (radical crosslinking reaction-curable) type. As the addition-curable type, it is possible to use one that contains diorganosiloxane having an alkenyl group(s), an MQ resin having an $R_3SiO_{0.5}$ unit and an $SiO_2$ unit, organohydrogenpolysiloxane having a plurality of SiH groups, a platinum catalyst, an addition reaction inhibitor, and an organic solvent, for example, described in JP 2015-193803A. As the radical curable type, it is possible to use one that contains diorganopolysiloxane with or without an alkenyl group, an MQ resin having an $R_3SiO_{0.5}$ unit and an $SiO_2$ unit, organic peroxide, and an organic solvent, for example, described in JP 2015-193803A. Herein, R represents a substituted or unsubstituted monovalent hydrocarbon group having 1 to 10 carbon atoms.

It is also possible to use a polysiloxane-resin integrated compound that is formed by condensation reaction of an MQ resin and polysiloxane having silanol at the terminal or the side chain of the polymer. The MQ resin contains many silanol and improves adhesion by addition of it, but does not bind to polysiloxane in molecular level because it is not crosslinkable. The adhesion can be increased by integrating the polysiloxane and the resin as described above.

The silicone resin may contain modified siloxane that has a group selected from an amino group, an oxirane group, an oxetane group, a polyether group, a hydroxy group, a carboxy group, a mercapto group, a methacryl group, an acryl group, a phenol group, a silanol group, a carboxylic anhydride group, an aryl group, an aralkyl group, an amide group, an ester group, and a lactone ring. The addition of modified siloxane improves dispersibility of the component (A) in the silicone resin. The modified siloxane may be modified at any part such as the one terminal, the both terminals, or the side chain of the siloxane.

When the polysilsesquioxane of the component (A) has a Q-unit, the component (A) alone makes it possible to improve adhesion similarly to MQ resin. Accordingly, addition of polysilsesquioxane of the component (A) makes it possible to secure adhesion without adding an MQ resin.

As the adherent acrylic base resin, it is possible to use one having hydrophilic (meth)acrylic ester and hydrophobic long chain (meth)acrylic ester as the repeating units described in JP 2016-011338A, for example. In some cases, it is also possible to copolymerize (meth)acrylic ester having a functional group or (meth)acrylic ester having a siloxane bond.

As the adherent urethane base resin, it is possible to use one having a urethane bond with a polyether bond, a polyester bond, a polycarbonate bond, or a siloxane bond described in JP 2016-065238A, for example.

In the inventive bio-electrode composition, the component (B) preferably has high compatibility with the component (A) to prevent lowering of the electric conductivity due to elution of the component (A) from the living body contact layer. In the inventive bio-electrode composition, the component (B) is preferably highly adhesive to the electro-conductive base material to prevent peeling of the living body contact layer from the electro-conductive base material. In order to increase the compatibility of the resin with the electro-conductive base material and the salt, the use of a resin with high polarity is effective. Illustrative examples of such a resin include resin having one or more moieties selected from an ether bond, an ester bond, an amide bond, an imide bond, a urethane bond, a thiourethane bond, and a thiol group, such as a polyacrylic resin, a polyamide resin, a polyimide resin, a polyurethane resin, and a polythiourethane resin. On the other hand, the living body contact layer is in contact with a living body, thereby being susceptible to perspiration. Accordingly, in the inventive bio-electrode composition, the component (B) preferably has high repellency, and is hardly hydrolyzed. To make the resin be highly repellent and hardly hydrolyzed, the use of a silicon-containing resin is effective.

The silicon atom-containing polyacrylic resin includes a polymer that has a silicone main chain and a polymer that has a silicon atom(s) on the side chain, each of which can be suitably used. As the polymer that has a silicone main chain, silsesquioxane or siloxane having a (meth)acrylpropyl group and so on can be used. In this case, an addition of a photoradical generator allows the (meth)acryl moiety to polymerize to cure.

As the silicon atom-containing polyamide resin, it is possible to suitably use polyamide silicone resins described in JP 2011-079946A and U.S. Pat. No. 5,981,680, for example. Such a polyamide silicone resin can be synthesized by combining a silicone or non-silicone compound having amino groups at the both terminals and a non-silicone or silicone compound having carboxy groups at the both terminals.

It is also possible to use polyamic acid before cyclization thereof, which is obtained by reacting carboxylic anhydride and amine. The carboxy group of the polyamic acid may be crosslinked by using a crosslinking agent such as an epoxy type and an oxetane type. It is also possible to esterify the carboxy group with hydroxyethyl (meth)acrylate to perform photoradical crosslinking of the (meth)acrylate moiety.

As the silicon atom-containing polyimide resin, it is possible to suitably use polyimide silicone resins described in JP 2002-332305A, for example. Although polyimide resins have very high viscosity, the viscosity can be decreased by blending a (meth)acrylic monomer as a solvent and a crosslinking agent.

Illustrative examples of the silicon atom-containing polyurethane resin include polyurethane silicone resins. These polyurethane silicone resins can be crosslinked through urethane bond by blending a compound having isocyanate groups at the both terminals and a compound having a hydroxy group(s) at the terminal(s), followed by heating thereof. In this case, a silicon atom(s) (siloxane bond) have to be contained in either or both of the compound having isocyanate groups at the both terminals and the compound having a hydroxy group(s) at the terminal(s). Alternatively, a urethane (meth)acrylate monomer and polysiloxane can be blended and photo-crosslinked as described in JP 2005-320418A. It is also possible to photo-crosslink a polymer having both of a siloxane bond(s) and a urethane bond(s), with the terminal having a (meth)acrylate group(s).

The silicon atom-containing polythiourethane resin can be obtained by reaction of a compound having a thiol group(s) and a compound having an isocyanate group(s), provided that either of them have to contain a silicon atom(s). It can also be photo-cured if (meth)acrylate groups are contained at the terminals.

The silicone base resin is improved in compatibility with the foregoing salt by adding modified siloxane that has a group selected from an amino group, an oxirane group, an oxetane group, a polyether group, a hydroxy group, a carboxy group, a mercapto group, a methacryl group, an acryl group, a phenol group, a silanol group, a carboxylic anhydride group, an aryl group, an aralkyl group, an amide group, an ester group, and a lactone ring in addition to the diorganosiloxane having an alkenyl group(s), the MQ resin having an $R_3SiO_{0.5}$ unit and an $SiO_2$ unit, and the organohydrogenpolysiloxane having a plurality of SiH groups.

As will be described later, the living body contact layer is a cured material of the bio-electrode composition. Curing the same improves the adhesion of the living body contact layer to both of skin and the electro-conductive base material. The curing means is not limited, and common means can be used, including crosslinking reaction by either or both of heat and light, an acid catalyst, or a base catalyst. The crosslinking reaction can be performed by appropriately selecting a crosslinking method described in "Kakyou hannou handbook (handbook of crosslinking reaction)", Chapter 2, pages 51-371, Yasuharu Nakamura, Maruzen shuppan (2013).

The diorganosiloxane having an alkenyl group(s) and organohydrogenpolysiloxane having a plurality of SiH groups can be crosslinked through an addition reaction with a platinum catalyst.

Illustrative examples of the platinum catalyst include platinum-based catalysts such as platinic chloride, alcohol solution of platinic chloride, reaction product of platinic chloride and alcohol, reaction product of platinic chloride and an olefin compound, reaction product of platinic chloride and vinyl group-containing siloxane, a platinum-olefin complex, a complex of platinum and vinyl group-containing siloxane; platinum group metal-based catalysts such as a rhodium complex and a ruthenium complex. These catalysts may be used after dissolved or dispersed in alcohol solvent, hydrocarbon solvent, or siloxane solvent.

The amount of platinum catalyst is preferably in a range of 5 to 2,000 ppm, particularly in a range of 10 to 500 ppm on the basis of 100 parts by mass of the resin.

When the addition curable silicone resin is used, an addition reaction inhibitor may be added. This addition reaction inhibitor is added as a quencher to prevent the platinum catalyst from acting in the solvent or under a low temperature circumstance after forming the coating film and before heat curing. Illustrative examples thereof include 3-methyl-1-butyn-3-ol, 3-methyl-1-pentyn-3-ol, 3,5-dimethyl-1-hexyn-3-ol, 1-ethynylcyclohexanol, 3-methyl-3-trimethylsilyloxy-1-butyne, 3-methyl-3-trimethylsiloxy-1-pentyne, 3,5-dimethyl-3-trimethylsiloxy-1-hexyne, 1-ethynyl-1-trimethylsiloxycyclohexane, bis(2,2-dimethyl-3-butynoxy)dimethylsilane, 1,3,5,7-tetramethyl-1,3,5,7-tetravinylcyclotetrasiloxane, and 1,1,3,3-tetramethyl-1, 3-divinyldisiloxane.

The amount of addition reaction inhibitor is preferably in a range of 0 to 10 parts by mass, particularly in a range of 0.05 to 3 parts by mass on the basis of 100 parts by mass of the resin.

Illustrative examples of photo-curing method include a method of adding a photoradical generator to generate radical by light, together with using a resin having a (meth)acrylate terminal(s) or an olefin terminal(s) or adding a crosslinking agent with the terminal(s) being (meth)acrylate, olefin, or a thiol group(s); and a method of adding a photo-acid generator to generate acid by light, together with using a resin or a crosslinking agent having an oxirane group(s), an oxetane group(s), or a vinyl ether group(s).

Illustrative examples of the photoradical generator include acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1,2'-biimidazole, methyl 2-benzoylbenzoic acid, 2-(1,3-benzodioxole-5-yl)-4,6-bis(trichloromethyl)-1,3,5-triazine, 2-benzyl-2-(dimethylamino)-4'-morpholinobutyrophenone, 4,4'-dichlorobenzophenone, 2,2-diethoxyacetophenone, 2,2-dimethoxy-2-phenylacetophenone, 2, 4-diethylthioxanthene-9-one, diphenyl(2,4,6-trimethylbenzoyl)phosphine oxide (BAPO), 1,4-dibenzoylbenzene, 2-ethylanthraquinone, 1-hydroxycyclohexyl phenyl ketone, 2-hydroxy-2-methylpropiophenone, 2-hydroxy-4'-(2-hydroxyethoxy)-2-methylpropiophenone, 2-isonitrosopropiophenone, and 2-phenyl-2-(p-toluenesulfonyloxy)acetophenone.

The curing can also be performed by adding a radical generator of a heat decomposition type. Illustrative examples of the thermal radical generator include 2,2'-azobis(isobutyronitrile), 2,2'-azobis(2,4-dimethylvaleronitrile), 2,2'-azobis(2-methylbutyronitrile), 2,2'-azobis(methylpropionamidine) hydrochloride, 2,2'-azobis[2-(2-imidazolin-2-yl)propane] hydrochloride, 2,2'-azobis(4-methoxy-2,4-dimethylvaleronitrile), 2,2'-azobis (cyclohexane-1-carbonitrile), 1[(1-cyano-1-methylethyl) azo]formamide, 2,2'-azobis[2-methyl-N-(2-hydroxyethyl) propionamide], 2,2'-azobis[N-(2-propenyl)-2-methylpropionamide], 2,2'-azobis(N-butyl-2-methylpropionamide), dimethyl-2,2'-azobis(isobutylate), 4,4'-azobis(4-cyanopentanoic acid), dimethyl-2,2'-azobis(2-methylpropionate), benzoyl peroxide, tert-butyl hydroperoxide, cumene hydroperoxide, di-tert-butyl peroxide, di-tert-amyl peroxide, di-n-butyl peroxide, and dicumyl peroxide.

Illustrative examples of the photo-acid generator include sulfonium salt, iodonium salt, sulfonyldiazomethane, N-sulfonyloxyimide, and oxime-O-sulfonate type acid generators. Specific examples of the photo-acid generator is described in paragraphs [0122] to [0142] of JP 2008-111103A, together with JP 2009-080474A.

The amount of radical generator or photo-acid generator is preferably in a range of 0.1 to 50 parts by mass on the basis of 100 parts by mass of the resin.

Among them, more preferable resin of the component (B) contains diorganosiloxane having an alkenyl group and organohydrogenpolysiloxane having an SiH group, and particularly preferable resin further contains a silicone resin having an $R_xSiO_{(4-x)/2}$ unit (wherein, R represents a substituted or unsubstituted monovalent hydrocarbon group having 1 to 10 carbon atoms, and "x" is a number in a range of 2.5 to 3.5) and an $SiO_2$ unit.

[Component (C)]

The inventive bio-electrode composition can further contain an electro-conductive powder as the component (C). The electro-conductive powder may be any powder having electric conductivity and is not particularly limited, but a carbon powder (carbon material) and a metal powder are preferable. The inventive bio-electrode composition contains the component (A) (silsesquioxane bonded to an N-carbonyl sulfonamide salt) as an ionic material (salt) and can be further improved in electric conductivity by adding these electro-conductive powders (carbon powder, metal powder). Incidentally, the electro-conductive powder is also referred to as "an electric conductivity improver" in the following.

[Carbon Powder]

As the electric conductivity improver, a carbon material (carbon powder) can be added. The carbon material may be exemplified by carbon black, carbon nanotube, carbon fiber, and the like. The carbon nanotube may be either single layer or multilayer, and the surface may be modified with an organic group(s). The amount of carbon material is preferably in a range of 1 to 50 parts by mass on the basis of 100 parts by mass of the resin.

[Metal Powder]

The inventive bio-electrode composition preferably contains a metal powder selected from gold, silver, platinum, copper, tin, titanium, nickel, aluminum, tungsten, molybdenum, ruthenium, chromium, and indium as the component (C) in order to improve electronic conductivity. The amount of the metal powder is preferably in a range of 1 to 50 parts by mass on the basis of 100 parts by mass of the resin.

As the kind of the metal powder, gold, silver, and platinum are preferable in view of electric conductivity; and silver, copper, tin, titanium, nickel, aluminum, tungsten, molybdenum, ruthenium, and chromium are preferable in view of cost. In view of biocompatibility, noble metals are preferable. On the whole of these viewpoints, silver is most preferable.

The metal powder may have any shape, such as a spherical shape, a disk shape, a flaky shape, and a needle shape. The addition of flaky powder brings highest electric conductivity and is preferable thereby. The metal powder is preferably a flake having relatively lower density and larger specific surface area with a size of 100 μm or less, a tapped density of 5 g/cm$^3$ or less, and a specific surface area of 0.5 m$^2$/g or more. It is also possible to add both of the metal powder and the carbon material (carbon powder) as the electric conductivity improver.

[Component (D)]

The inventive bio-electrode composition can further contain an additive(s) as a component (D) in accordance with needs. The additive may be any material other than the components (A) to (C) and is not particularly limited. Illustrative examples thereof include a component that can improve the stretchability or adhesion of a cured material of the bio-electrode composition, such as a tackifier; a component to promote the curing reaction, such as a radical generator and a platinum catalyst; and a component to facilitate the handling of a bio-electrode composition, such as an organic solvent. Hereinafter, the component (D) will be described specifically.

[Tackifier]

The inventive bio-electrode composition may contain a tackifier in order to have adhesion to a living body. Illustrative examples of such a tackifier include silicone resin, as well as non-crosslinkable siloxane, non-crosslinkable poly(meth)acrylate, and non-crosslinkable polyether. The inventive bio-electrode composition can contain an adhesive resin as the component (B) in accordance with needs and has more preferable adhesion to a living body by adding the tackifier like this.

[Organic Solvent]

The inventive bio-electrode composition may contain an organic solvent. Illustrative examples of the organic solvent include aromatic hydrocarbon solvent such as toluene, xylene, cumene, 1,2,3-trimethylbenzene, 1,2,4-trimethylbenzene, 1,3,5-trimethylbenzene, styrene, a-methylstyrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethyltoluene, 1,2,4,5-tetramethyltoluene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, pentamethylbenzene, hexamethylbenzene, hexylbenzene, and 1,3,5-triethylbenzene; aliphatic hydrocarbon solvent such as n-heptane, isoheptane, 3-methylhexane, 2,3-dimethylpentane, 3-ethylpentane, 1,6-heptadiene, 5-methyl-1-hexyn, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.0$^{2,7}$]undeca-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, and isoparaffin; ketone solvent such as cyclohexanone, cyclopentanone, 2-octanone, 2-nonanone, 2-heptanone, 3-heptanone, 4-heptanone, 2-hexanone, 3-hexanone, diisobutyl ketone, methylcyclohexanone, and methyl n-pentyl ketone; alcohol solvent such as 3-methoxybutanol, 3-methyl-3-methoxybutanol, 1-methoxy-2-propanol, and 1-ethoxy-2-propanol; ether solvent such as propylene glycol monomethyl ether, ethylene glycol monomethyl ether, propylene glycol monoethyl ether, ethylene glycol monoethyl ether, propylene glycol dimethyl ether, diethylene glycol dimethyl ether, diisopropyl ether, diisobutyl ether, diisopentyl ether, di-n-pentyl ether, methyl cyclopentyl ether, methyl cyclohexyl ether, di-n-butyl ether, di-sec-butyl ether, di-sec-pentyl ether, di-tert-amyl ether, di-n-hexyl ether, and anisole; ester solvent such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate; lactone solvent such as y-butyrolactone.

The amount of organic solvent is preferably in a range of 10 to 50,000 parts by mass on the basis of 100 parts by mass of the resin. The inventive bio-electrode composition is more improved in coating property by containing an organic solvent as the component (D).

As described above, the inventive bio-electrode composition makes it possible to form a living body contact layer for a bio-electrode that is capable of conducting electric signals from skin efficiently to a device (i.e., excellent in electric conductivity), free from the risk of causing allergies even when it is worn on skin for a long time (i.e., excellent in biocompatibility), light-weight, manufacturable at low cost, and free from large lowering of the electric conductivity even though it is wetted with water or dried. It is possible to improve the electric conductivity still more by adding an electro-conductive powder (carbon powder, metal powder), and to manufacture a bio-electrode with particularly high adhesion and stretchability by combining a resin with adhesion and stretchability. Furthermore, it is possible to improve the stretchability and adhesion to skin using additives, and to control the stretchability and adhesion by adjusting the composition of the resin and the thickness of the living body contact layer appropriately.

<Bio-Electrode>

The present invention also provides a bio-electrode comprising an electro-conductive base material and a living body contact layer formed on the electro-conductive base material; wherein the living body contact layer is a cured material of the inventive bio-electrode composition described above.

Hereinafter, the inventive bio-electrode will be specifically described by reference to the FIGS., but the present invention is not limited thereto.

FIG. 1 is a schematic sectional view showing an example of the inventive bio-electrode. The bio-electrode 1 of FIG. 1 has the electro-conductive base material 2 and the living body contact layer 3 formed on the electro-conductive base material 2. The living body contact layer 3 is composed of a cured material of the inventive bio-electrode composition. The ionic silsesquioxane (SSQ) material 4 composing the living body contact layer 3 contains a cured material of the N-carbonyl sulfonamide salt-silsesquioxane. The living body contact layer 3 can also contain the resin 6 other than the ionic SSQ material 4 and/or an electro-conductive powder (the metal powder 5a, the carbon powder 5b; hereinafter, they are also referred to as a general term of "the electro-conductive powder 5"). Hereinafter, the living body contact layer 3 is described as a layer in which the ionic silicone material 4 and the electro-conductive powder 5 are dispersed in the resin 6 by referring FIGS. 1 and 2, but the inventive bio-electrode is not limited to this embodiment. Incidentally, 5b in the figures represents carbon nanotube.

In using the bio-electrode 1 of FIG. 1 like this, electric signals are picked from the living body 7 through the ionic SSQ material 4 and the electro-conductive powder 5 while bringing the living body contact layer 3 (i.e., the layer in which the ionic SSQ material 4 and the electro-conductive powder 5 are dispersed in the resin 6) into contact with the living body 7, and then conducted to a sensor device (not shown) through the electro-conductive base material 2 as shown in FIG. 2. As described above, the inventive bio-electrode is capable of coping with both electric conductivity and biocompatibility by using the ionic SSQ material described above and obtaining electric signals from skin stably in high sensitivity because the contact area with skin is kept constant due to the adhesion thereof.

Hereinafter, each component composing the inventive bio-electrode will be described more specifically.

[Electro-Conductive Base Material]

The inventive bio-electrode comprises an electro-conductive base material. This electro-conductive base material is usually connected electrically with a sensor device and so on, and conducts electrical signals picked from a living body through the living body contact layer to the sensor device and so on.

As the electro-conductive base material, any electro-conductive material can be used without being limited to particular ones. However, it is preferable to comprise one or more species selected from gold, silver, silver chloride, platinum, aluminum, magnesium, tin, tungsten, iron, copper, nickel, stainless steel, chromium, titanium, carbon, and an electro-conductive polymer, for example.

The electro-conductive base material may be a hard electro-conductive substrate, an electro-conductive film having flexibility, a cloth with the surface being coated with electro-conductive paste, or a cloth into which electro-conductive polymer is kneaded without being limited to particular substrates. The electro-conductive base material may be flat, uneven, or mesh-form of woven metal wires, which can be appropriately selected in accordance with the use of the bio-electrode.

[Living Body Contact Layer]

The inventive bio-electrode comprises a living body contact layer formed on the electro-conductive base material. This living body contact layer is a part to be actually in contact with a living body when using the bio-electrode, and has electric conductivity and adhesion. The living body contact layer is a cured material of the inventive bio-electrode composition described above, that is to say, an adherent resin layer composed of a cured material of a composition containing the component (A), together with the component (B), the component (C), and the component (D) in accordance with needs.

The living body contact layer preferably has adhesion in a range of 0.5 N/25 mm or more and 20 N/25 mm or less. The adhesion is commonly measured by the method shown in JIS Z 0237, in which a metal substrate such as a stainless steel (SUS) substrate or a polyethylene terephthalate (PET) substrate can be used as a base material or, alternatively, human skin can be used for measuring. Human skin has lower surface energy compared to metals and various plastics, which energy is as low as that of Teflon (registered trade mark), and is hard to adhere.

The living body contact layer of the bio-electrode preferably has a thickness of 1 μm or more and 5 mm or less, more preferably 2 μm or more and 3 mm or less. As the living body contact layer is thinner, the adhesion lowers, but the flexibility is improved, and the weight decreases to improve the compatibility with skin. The thickness of the living body contact layer can be selected based on the balance of adhesion and texture.

The inventive bio-electrode may be provided with an adherent film separately on the living body contact layer as previous bio-electrodes (e.g., the bio-electrode described in JP 2004-033468A) in order to prevent peeling off of the bio-electrode from a living body during the use. When the adherent film is prepared separately, the adherent film may be formed by using a raw material for the adherent film such as an acrylic type, a urethane type, and a silicone type. Particularly, the silicone type is suitable because of the high transparency of oxygen, which enables cutaneous respiration while pasting the same, the high water repellency, which decreases lowering of adhesion due to perspiration, and the low irritation to skin. It is to be noted that the inventive bio-electrode does not necessarily require the adherent film that is prepared separately described above, because peeling off from a living body can be prevented by adding tackifier to the bio-electrode composition or using a resin having good adhesion to a living body as described above.

When the inventive bio-electrode is used as a wearable device, wiring between the bio-electrode and a sensor device, and other components are not limited to particular ones. For example, it is possible to apply the ones described in JP 2004-033468A.

As described above, the inventive bio-electrode is capable of conducting electric signals from skin efficiently to a device (i.e., excellent in electric conductivity), free from the risk of causing allergies even when it is worn on skin for a long time (i.e., excellent in biocompatibility), light-weight, manufacturable at low cost, and free from large lowering of the electric conductivity even though it is wetted with water or dried, because the living body contact layer is formed from a cured material of the inventive bio-electrode composition described above. It is possible to improve the electric conductivity still more by adding an electro-conductive powder, and to manufacture a bio-electrode with higher adhesion and stretchability by combining a resin that has adhesion and stretchability. It is also possible to improve the stretchability and adhesion to skin using additives, and to control the stretchability and adhesion by adjusting the composition of the resin and the thickness of the living body contact layer appropriately. Accordingly, the inventive bio-electrode described above is particularly suitable as a bio-electrode used for a medical wearable device.

<Method for Manufacturing Bio-Electrode>

The present invention also provides a method for manufacturing a bio-electrode having an electro-conductive base material and a living body contact layer formed on the electro-conductive base material, comprising: applying the inventive bio-electrode composition described above onto the electro-conductive base material; and curing the bio-electrode composition; thereby forming the living body contact layer.

Incidentally, the electro-conductive base material, etc. used for the inventive method for manufacturing a bio-electrode may be the same as those described above.

The method for applying the bio-electrode composition onto the electro-conductive base material is not limited to particular ones; and dip coating, spray coating, spin coating, roll coating, flow coating, doctor coating, screen printing, flexographic printing, gravure printing, and inkjet printing are suitable, for example.

The method for curing the resin can be appropriately selected based on the components (A) and (B) used for the bio-electrode composition without being limited to particular methods. For example, the bio-electrode composition is preferably cured by either or both of heat and light. The foregoing bio-electrode composition can also be cured by adding a catalyst to generate acid or base to the bio-electrode composition, which causes a crosslinking reaction.

In case of heating, the temperature is not particularly limited and may be appropriately selected based on the components (A) and (B) used for the bio-electrode composition, but is preferably about 50 to 250° C., for example.

When the heating and light irradiation are combined, it is possible to perform the heating and the light irradiation simultaneously, to perform the heating after the light irradiation, or to perform the light irradiation after the heating. It is also possible to perform air-drying to evaporate the solvent before heating the coating film.

As described above, the inventive method for manufacturing a bio-electrode makes it possible to manufacture the inventive bio-electrode easily and at low cost, with the bio-electrode being excellent in electric conductivity and biocompatibility, light-weight, and free from large lowering of the electric conductivity even though it is wetted with water or dried.

EXAMPLE

Hereinafter, the present invention will be specifically described by giving Examples and Comparative Examples, but the present invention is not limited thereto. Incidentally, "Me" represents a methyl group, and "Vi" represents a vinyl group.

An N-carbonyl sulfonamide salt-trialkoxysilane compound was synthesized by mixing an N-carbonyl sulfonamide salt having a double bond, an ether compound having a double bond in accordance with needs, a trialkoxysilane compound having an SiH group, and a platinum catalyst in a mixed solvent of toluene and PGMEA in 1:1, followed by heating at 60° C. for 2 hours. After drying the solvent, the composition was identified by $^1$H-NMR. This alkoxysilane compound was (co-) condensed, together with another alkoxysilane compound or alkoxide of metal other than silicon in accordance with needs, to give a polymer of N-carbonyl sulfonamide salt-silsesquioxane (hereinafter, also referred to as "N-carbonyl sulfonamide salt-SSQ"). The weight average molecular weight (Mw) and the dispersity (Mw/Mn) of this polymer were determined by gel permeation chromatography (GPC) using tetrahydrofuran (THF) as a solvent. Thus synthesized N-carbonyl sulfonamide salt-trialkoxysilane compound 1 and N-carbonyl sulfonamide salt-SSQs 1 to 9 are shown below.

N-Carbonyl Sulfonamide Salt-Trialkoxysilane Compound 1

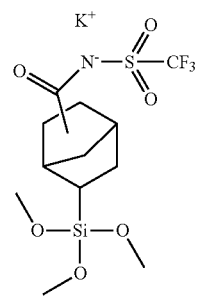

Into a 1 L glass flask, 200 g of methanol, 200 g of pure water, and 1 g of 35% hydrochloric acid were introduced, and 0.5 mol of N-carbonyl sulfonamide salt-trialkoxysilane compound 1 and 0.5 mol of tetramethoxysilane were added thereto at room temperature over 1 hour. This was stirred at room temperature for 8 hours, and 300 g of propylene glycol monoethyl ether (PGEE) was added thereto. This was concentrated under reduced pressure to give a solution containing 30 mass % of N-carbonyl sulfonamide salt-silsesquioxane 1 in PGEE.

N-Carbonyl Sulfonamide Salt-SSQ 1
Mw=4,100
Mw/Mn=4.90

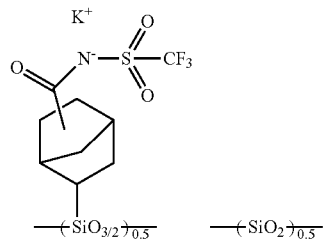

In the same way as described above, trialkoxysilane bonded to an N-carbonyl sulfonamide salt and other alkoxysilanes were condensed to give a solution containing 30 mass % of the following N-carbonyl sulfonamide salt-SSQ 2 in PGEE.

N-Carbonyl Sulfonamide Salt-SSQ 2
Mw=5,800
Mw/Mn=3.31

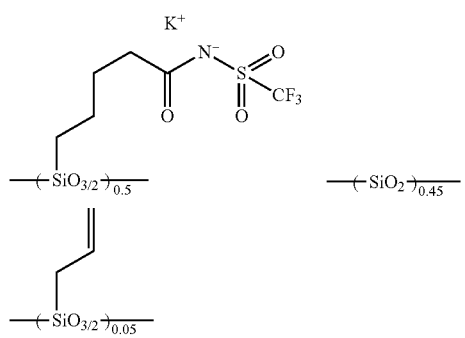

In the same way as described above, trialkoxysilane bonded to an N-carbonyl sulfonamide salt and other alkoxysilanes were condensed to give a solution containing 30 mass % of the following N-carbonyl sulfonamide salt-SSQ 3 in PGEE.

N-Carbonyl Sulfonamide Salt-SSQ 3
Mw=3,100
Mw/Mn=2.97

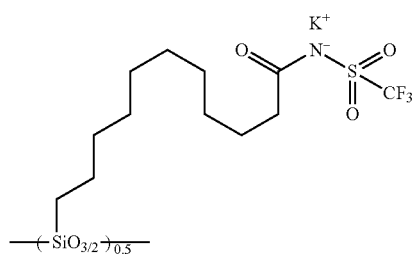

-continued

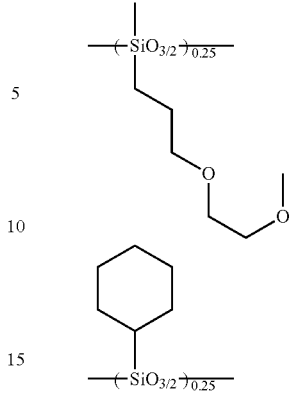

In the same way as described above, trialkoxysilane bonded to an N-carbonyl sulfonamide salt and other alkoxysilanes were condensed to give a solution containing 30 mass % of the following N-carbonyl sulfonamide salt-SSQ 4 in PGEE.

N-Carbonyl Sulfonamide Salt-SSQ 4
Mw=3,300
Mw/Mn=3.22

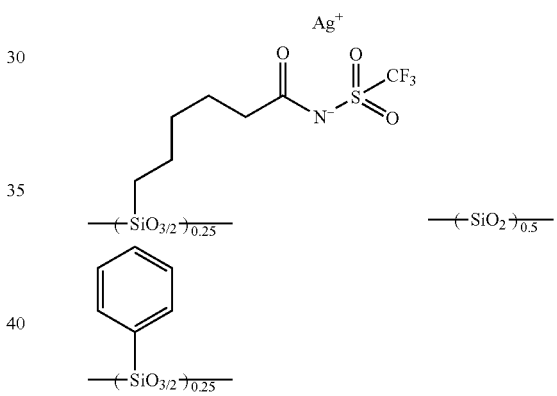

In the same way as described above, trialkoxysilane bonded to an N-carbonyl sulfonamide salt and other alkoxysilanes were condensed to give a solution containing 30 mass % of the following N-carbonyl sulfonamide salt-SSQ 5 in PGEE.

N-Carbonyl Sulfonamide Salt-SSQ 5
Mw=3,500
Mw/Mn=3.86

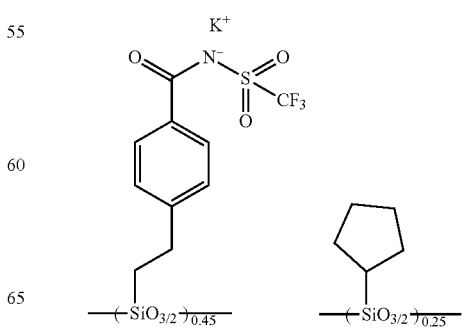

-continued

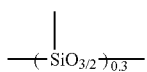

In the same way as described above, trialkoxysilane bonded to an N-carbonyl sulfonamide salt and other alkoxysilanes were condensed to give a solution containing 30 mass % of the following N-carbonyl sulfonamide salt-SSQ 6 in PGEE.

N-Carbonyl Sulfonamide Salt-SSQ 6
Mw=4,800
Mw/Mn=4.30

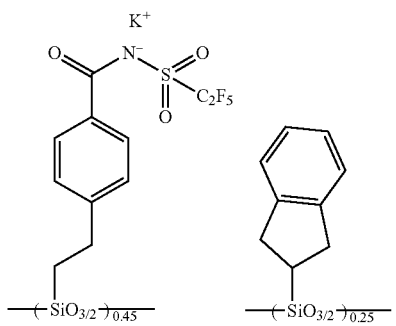

In the same way as described above, trialkoxysilane bonded to an N-carbonyl sulfonamide salt and other alkoxysilanes were condensed to give a solution containing 30 mass % of the following N-carbonyl sulfonamide salt-SSQ 7 in PGEE.

N-Carbonyl Sulfonamide Salt-SSQ 7
Mw=3,700
Mw/Mn=3.99

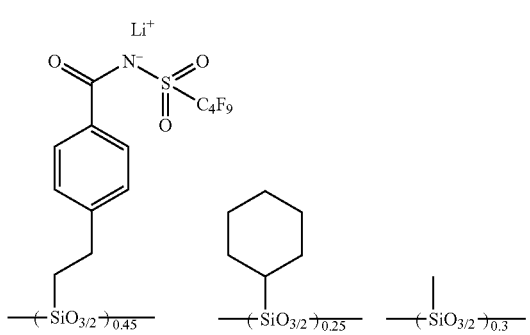

In the same way as described above, trialkoxysilane bonded to an N-carbonyl sulfonamide salt, another alkoxysilane, and titanium n-butoxide were condensed to give a solution containing 30 mass % of the following N-carbonyl sulfonamide salt-SSQ 8 in PGEE.

N-Carbonyl Sulfonamide Salt-SSQ 8
Mw=3,500
Mw/Mn=3.86

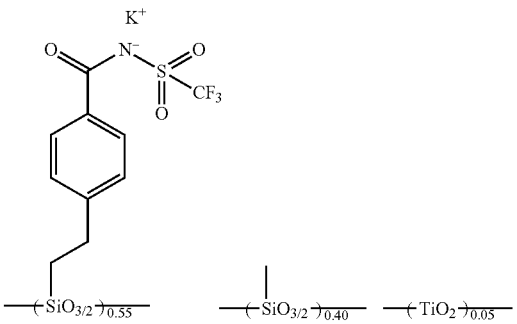

In the same way as described above, trialkoxysilane bonded to an N-carbonyl sulfonamide salt and other alkoxysilanes were condensed to give a solution containing 30 mass % of the following N-carbonyl sulfonamide salt-SSQ 9 in PGEE.

N-Carbonyl Sulfonamide Salt-SSQ 9
Mw=4,500
Mw/Mn=3.44

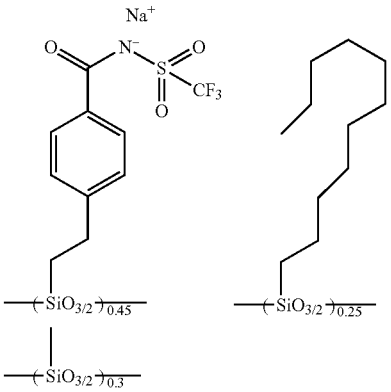

Comparative salts 1 to 4, which were blended as an ionic material to the bio-electrode composition solutions of Comparative Examples, are shown below.

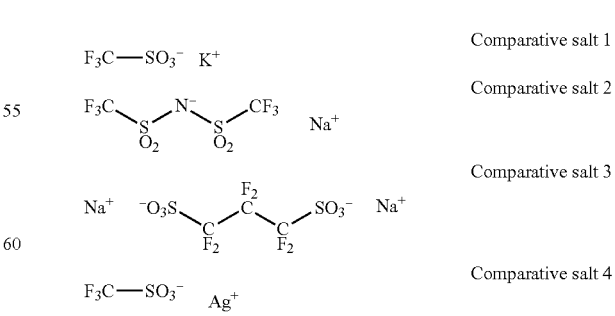

Siloxane compounds 1 to 4, which were blended to the bio-electrode composition solutions as a silicone base resin, are shown below.

(Siloxane Compound 1)

Siloxane compound 1 was vinyl group-containing polydimethylsiloxane having an alkenyl group-content of 0.007 mol/100 g in which the terminals of molecular chain were blocked with $SiMe_2Vi$ groups, with the 30% toluene solution having a viscosity of 27,000 mPa·s.

(Siloxane Compound 2)

Siloxane compound 2 was a 60% toluene solution of polysiloxane of MQ resin composed of an $Me_3SiO_{0.5}$ unit and an $SiO_2$ unit ($Me_2SiO_{0.5}$ unit/$SiO_2$ unit=0.8).

(Siloxane Compound 3)

Siloxane compound 3 was a polydimethylsiloxane-bonded MQ resin obtained by heating a solution composed of 40 parts by mass of vinyl group-containing polydimethylsiloxane having an alkenyl group-content of 0.007 mol/100 g in which the terminals of molecular chain were blocked with OH groups, with the 30% toluene solution having a viscosity of 42,000 mPa·s; 100 parts by mass of 60% toluene solution of polysiloxane of MQ resin composed of an $Me_2SiO_{0.5}$ unit and an $SiO_2$ unit ($Me_2SiO_{0.5}$ unit/$SiO_2$ unit=0.8); and 26.7 parts by mass of toluene with refluxing for 4 hours, followed by cooling.

(Siloxane Compound 4)

As methylhydrogensilicone oil, KF-99 manufactured by Shin-Etsu Chemical Co., Ltd. was used.

As a silicone base resin, KF-353 manufactured by Shin-Etsu Chemical Co., Ltd. was used, which is polyether type silicone oil with the side chain being modified with polyether.

Acrylic polymer blended as an acrylic base resin to the bio-electrode composition solution is shown below.

Acrylic Polymer 1
Mw=108,000
Mw/Mn=2.32

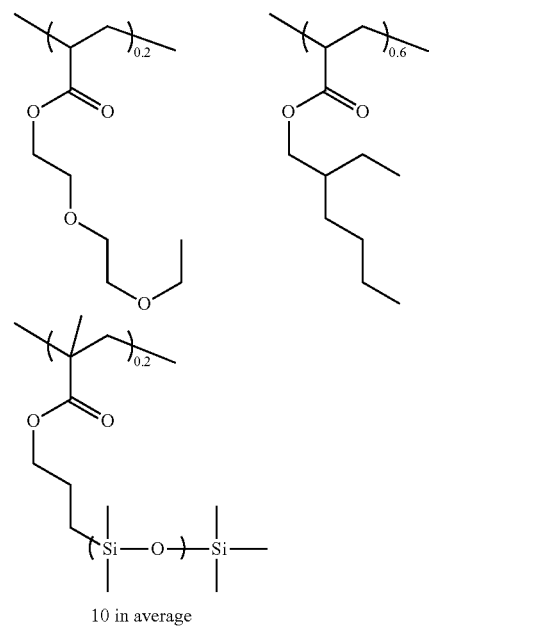

Acrylic Polymer 1

The repeating number in the formula shows the average value.

Silicone-urethane acrylates 1 and 2, which were blended to the bio-electrode composition solutions as a silicone base, acrylic base, or urethane base resin, are shown below.

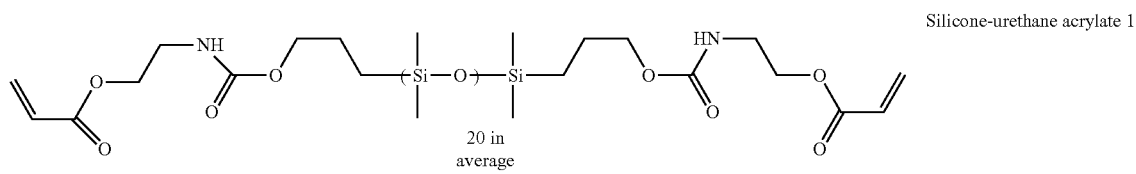

Silicone-urethane acrylate 1

Silicone-urethane acrylate 2

The repeating number in the formula shows the average value.

Organic solvents, which were blended to the bio-electrode composition solutions, are shown below.
PGMEA: propylene glycol-1-monomethyl ether-2-acetate
PGME: propylene glycol-1-monomethyl ether
PGEE: propylene glycol-1-monoethyl ether
ISOPAR E: isoparaffin base solvent, manufactured by Standard Sekiyu CO., LTD
ISOPAR G: isoparaffin base solvent, manufactured by Standard Sekiyu CO., LTD The following are metal powders, a radical generator, a platinum catalyst, and electric conductivity improvers (carbon black and carbon nanotube) blended to the bio-electrode composition solution as an additive.
Metal Powders:
Silver powder: silver flake manufactured by Sigma-Aldrich Co. LLC., with the diameter of 10 μm
Gold powder: gold powder manufactured by Sigma-Aldrich Co. LLC., with the diameter of 10 μm or less
Radical generator: V-601 manufactured by FUJI FILM Wako Pure Chemical Corporation
Platinum catalyst: CAT-PL-50T manufactured by Shin-Etsu Chemical Co., Ltd.
Carbon black: DENKA BLACK HS-100 manufactured by Denka Co., Ltd.
Multilayer carbon nanotube: manufactured by Sigma-Aldrich Co. LLC., with the diameter of 110 to 170 nm and the length of 5 to 9 μm Examples 1 to 15, Comparative Examples 1 to 5

On the basis of each composition described in Table 1 and Table 2, the ionic material (salt), the resin (adhesive resin), the organic solvent, and the other additives (radical generator, platinum catalyst, electric conductivity improver) were blended to prepare each bio-electrode composition solution (Bio-electrode composition solutions 1 to 15, Comparative bio-electrode composition solutions 1 to 5).

TABLE 1

| Bio-electrode composition solution | Ionic material (parts by mass) | Resins (parts by mass) | Organic solvent (parts by mass) | Additives (parts by mass) |
|---|---|---|---|---|
| Bio-electrode composition solution 1 | N-carbonyl sulfonamide salt-SSQ 1 (60) | Siloxane compound 1 (40) KF-99 (2.5) KF-353 (10) | toluene (30) | CAT-PL-50T (1.5) Carbon black (10) |
| Bio-electrode composition solution 2 | N-carbonyl sulfonamide salt-SSQ 2 (30) | Siloxane compound 3 (126) KF-99 (2.5) KF-353 (10) | heptane (30) PGMEA (14) | CAT-PL-50T (0.7) Carbon black (10) |
| Bio-electrode composition solution 3 | N-carbonyl sulfonamide salt-SSQ 3 (30) | Siloxane compound 1 (40) Siloxane compound 2 (50) KF-99 (2.5) | ISOPAR E (30) PGMEA (14) | CAT-PL-50T (0.7) Carbon black (10) |
| Bio-electrode composition solution 4 | N-carbonyl sulfonamide salt-SSQ 4 (30) | Siloxane compound 1 (40) Siloxane compound 2 (60) KF-99 (2.5) KF-353 (10) | ISOPAR G (30) PGMEA (14) | CAT-PL-50T (0.7) Carbon black (10) |
| Bio-electrode composition solution 5 | N-carbonyl sulfonamide salt-SSQ 5 (30) | Siloxane compound 3 (126) KF-99 (2.5) KF-353 (10) | toluene (44) | CAT-PL-50T (1.0) Carbon black (10) |
| Bio-electrode composition solution 6 | N-carbonyl sulfonamide salt-SSQ 6 (30) | Siloxane compound 1 (40) Siloxane compound 2 (60) KF-99 (2.5) KF-353 (26) | toluene (30) 2-heptanone (14) | CAT-PL-50T (2.0) Carbon black (10) |
| Bio-electrode composition solution 7 | N-carbonyl sulfonamide salt-SSQ 7 (35) | Siloxane compound 1 (40) Siloxane compound 2 (60) KF-99 (2.5) KF-353 (26) | toluene (30) 2-heptanone (14) | CAT-PL-50T (2.0) Carbon black (10) |
| Bio-electrode composition solution 8 | N-carbonyl sulfonamide salt-SSQ 8 (43) | Siloxane compound 1 (40) Siloxane compound 2 (50) KF-99 (2.5) KF-353 (26) | toluene (30) 2-heptanone (14) | CAT-PL-50T (2.0) Carbon black (10) |
| Bio-electrode composition solution 9 | N-carbonyl sulfonamide salt-SSQ 9 (43) | Siloxane compound 1 (40) Siloxane compound 2 (50) KF-99 (2.5) KF-353 (26) | toluene (30) 2-heptanone (14) | CAT-PL-50T (2.0) Carbon black (10) |
| Bio-electrode composition solution 10 | N-carbonyl sulfonamide salt-SSQ 3 (30) N-carbonyl sulfonamide salt-SSQ 5 (20) | Siloxane compound 1 (40) Siloxane compound 2 (50) KF-99 (2.5) KF-353 (26) | toluene (30) 2-heptanone (14) | CAT-PL-50T (2.0) Carbon black (10) |
| Bio-electrode composition solution 11 | N-carbonyl sulfonamide salt-SSQ 5 (30) | Siloxane compound 1 (40) Siloxane compound 2 (100) KF-99 (2.5) KF-353 (26) | toluene (30) PGME (14) | CAT-PL-50T (1.5) Silver powder (5) Carbon black (5) |
| Bio-electrode composition solution 12 | N-carbonyl sulfonamide salt-SSQ 5 (30) | Siloxane compound 1 (40) Siloxane compound 2 (100) KF-99 (2.5) KF-353 (26) | toluene (30) PGEE (14) | CAT-PL-50T (1.5) Silver powder (5) Multilayer carbon nanotube (3) |

TABLE 2

| Bio-electrode composition solution | Ionic material (parts by mass) | Resins (parts by mass) | Organic solvent (parts by mass) | Additives (parts by mass) |
|---|---|---|---|---|
| Bio-electrode composition solution 13 | N-carbonyl sulfonamide salt-SSQ 5 (30) | Acrylic polymer 1 (60) Silicone-urethane acrylate 1 (20) | PGMEA (100) | Radical generator V-601 (4) Silver powder (10) |
| Bio-electrode composition solution 14 | N-carbonyl sulfonamide salt-SSQ 5 (30) | Acrylic polymer 1 (55) Silicone-urethane acrylate 1 (25) | PGMEA (100) | Radical generator V-601 (4) Gold powder (10) |
| Bio-electrode composition solution 15 | N-carbonyl sulfonamide salt-SSQ 5 (30) | Acrylic polymer 1 (60) Silicone-urethane acrylate 2 (20) | PGMEA (100) | Radical generator V-601 (4) Silver powder (10) |
| Comparative bio-electrode composition solution 1 | Comparative salt 1 (4.7) | Siloxane compound 3 (126) KF-99 (2.5) KF-353 (10) | toluene (30) PGME (14) | CAT-PL-50T (1.5) Carbon black (10) |
| Comparative bio-electrode composition solution 2 | Comparative salt 2 (8.2) | Siloxane compound 3 (126) KF-99 (2.5) KF-353 (10) | toluene (30) PGME (14) | CAT-PL-50T (1.5) Carbon black (10) |
| Comparative bio-electrode composition solution 3 | Comparative salt 3 (8.4) | Siloxane compound 3 (126) KF-99 (2.5) KF-353 (10) | toluene (30) PGME (14) | CAT-PL-50T (1.5) Carbon black (10) |
| Comparative bio-electrode composition solution 4 | Comparative salt 4 (8.4) | Siloxane compound 3 (126) KF-99 (2.5) KF-353 (10) | toluene (30) PGME (14) | CAT-PL-50T (1.5) Carbon black (10) |
| Comparative bio-electrode composition solution 5 | — | Siloxane compound 3 (126) KF-99 (2.5) KF-353 (10) | toluene (30) PGME (14) | CAT-PL-50T (1.5) Carbon black (10) |

(Evaluation of Electric Conductivity)

Each bio-electrode composition solution was applied onto an aluminum disk having a diameter of 3 cm and a thickness of 0.2 mm by using an applicator. This was air-dried at room temperature for 6 hours and then baked at 120° C. for 30 minutes under a nitrogen atmosphere by using an oven to be cured, thereby producing four pieces of bio-electrodes for each bio-electrode composition solution. Thus obtained bio-electrode had the living body contact layer 3 at one side and the aluminum disk 8 at the other side as an electro-conductive base material as shown in FIGS. 3A and 3B. Then, the copper wiring 9 was pasted on the surface of the aluminum disk 8 with self-adhesive tape at the side that had not been coated with the living body contact layer to form a lead-out electrode, which was connected to an impedance measurement apparatus as shown in FIG. 3B. Two pieces of the bio-electrodes 1' were pasted on a human arm at a distance of 15 cm from each other such that the side of each living body contact layer was in contact with the skin of the human arm as shown in FIG. 4. The initial impedance was measured while altering the frequency by using an AC impedance measurement apparatus SI1260 manufactured by Solartron. Then, the remained two pieces of the bio-electrodes were immersed in pure water for 1 hour, and used for measuring the impedance on skin by the same method described above after drying the water. Each impedance at the frequency of 1,000 Hz is shown in Table 3.

(Evaluation of Adhesion)

Each bio-electrode composition solution was applied onto a polyethylene naphthalate (PEN) substrate having a thickness of 100 μm by using an applicator. This was air dried at room temperature for 6 hours, followed by curing through baking at 120° C. for 30 minutes under a nitrogen atmosphere by using an oven to produce an adhesive film. From this adhesive film, a tape with a width of 25 mm was cut out. This was pressed to a stainless (SUS304) board and allowed to stand at room temperature for 20 hours. Then, the force (N/25 mm) for peeling the tape, which had been produced from the adhesive film, from the stainless board was measured at an angle of 180° and a speed of 300 ram/min by using a tensile tester. The results are shown in Table 3.

(Measurement of Thickness of Living Body Contact Layer)

On each bio-electrode produced in the evaluation test of electric conductivity described above, the thickness of the living body contact layer was measured by using a micrometer. The results are shown in Table 3.

TABLE 3

| Example | Bio-electrode composition solution | Adhesion (N/25 mm) | Thickness of resin (μm) | Initial impedance ($\Omega$) | Impedance after water immersion ($\Omega$) |
|---|---|---|---|---|---|
| Example 1 | Bio-electrode composition solution 1 | 3.6 | 450 | $7.1E^4$ | $7.3E^4$ |
| Example 2 | Bio-electrode composition solution 2 | 4.8 | 490 | $6.8E^4$ | $6.5E^4$ |
| Example 3 | Bio-electrode composition solution 3 | 4.2 | 480 | $1.1E^4$ | $1.0E^4$ |
| Example 4 | Bio-electrode composition solution 4 | 4.5 | 390 | $8.1E^4$ | $8.2E^4$ |

TABLE 3-continued

| Example | Bio-electrode composition solution | Adhesion (N/25 mm) | Thickness of resin (μm) | Initial impedance (Ω) | Impedance after water immersion (Ω) |
|---|---|---|---|---|---|
| Example 5 | Bio-electrode composition solution 5 | 3.9 | 440 | $3.1E^4$ | $4.9E^4$ |
| Example 6 | Bio-electrode composition solution 6 | 3.8 | 510 | $3.8E^4$ | $3.1E^4$ |
| Example 7 | Bio-electrode composition solution 7 | 4.3 | 460 | $2.3E^4$ | $3.6E^4$ |
| Example 8 | Bio-electrode composition solution 8 | 4.3 | 350 | $2.5E^4$ | $3.1E^4$ |
| Example 9 | Bio-electrode composition solution 9 | 4.5 | 510 | $2.5E^4$ | $2.8E^4$ |
| Example 10 | Bio-electrode composition solution 10 | 4.5 | 460 | $3.7E^4$ | $4.4E^4$ |
| Example 11 | Bio-electrode composition solution 11 | 4.3 | 490 | $4.7E^4$ | $5.1E^4$ |
| Example 12 | Bio-electrode composition solution 12 | 4.4 | 550 | $6.2E^4$ | $7.0E^4$ |
| Example 13 | Bio-electrode composition solution 13 | 3.1 | 310 | $8.4E^4$ | $9.1E^4$ |
| Example 14 | Bio-electrode composition solution 14 | 3.4 | 350 | $8.8E^4$ | $8.7E^4$ |
| Example 15 | Bio-electrode composition solution 15 | 3.2 | 410 | $8.9E^4$ | $8.6E^4$ |
| Comparative Example 1 | Comparative bio-electrode composition solution 1 | 3.3 | 520 | $4.2E^4$ | $5.3E^5$ |
| Comparative Example 2 | Comparative bio-electrode composition solution 2 | 3.2 | 530 | $8.2E^4$ | $7.3E^5$ |
| Comparative Example 3 | Comparative bio-electrode composition solution 3 | 3.6 | 520 | $7.1E^4$ | $9.3E^5$ |
| Comparative Example 4 | Comparative bio-electrode composition solution 4 | 3.6 | 560 | $1.1E^5$ | $1.1E^6$ |
| Comparative Example 5 | Comparative bio-electrode composition solution 5 | 3.9 | 530 | $1.9E^7$ | $2.8E^7$ |

As shown in Table 3, in each of Examples 1 to 15, the living body contact layer of which was formed by using the inventive bio-electrode composition containing a sulfonamide salt silicone compound and resins, the initial impedance was low, and the impedance did not cause large change after the bio-electrodes were immersed to water and dried. That is, Examples 1 to 15 each gave a bio-electrode that had high initial electric conductivity and did not cause large lowering of the electric conductivity even though it was wetted with water or dried. These bio-electrodes of Examples 1 to 15 had good adhesion similar to that of bio-electrode of Comparative Examples 1 to 5, in which previous salt and resin were blended, and was light-weight, excellent in biocompatibility, and manufacturable at low cost.

On the other hand, in each Comparative Examples 1 to 4, the living body contact layer of which was formed by using a bio-electrode composition containing previous salt and resins, the initial impedance was low, but large increase of the impedance occurred such that the order of magnitude was changed after water immersion and drying. That is, each of Comparative Examples 1 to 4 only gave a bio-electrode, the electric conductivity of which was largely decreased when it was wetted with water and dried, although the initial electric conductivity was high.

Comparative Example 5, in which the living body contact layer was formed by using a bio-electrode composition that contained resins without containing salt, did not cause large increase of impedance by an order of magnitude after it was immersed to water and dried because it did not contain salt, but the initial impedance was high. That is, Comparative Example 5 only gave a bio-electrode with low initial electric conductivity.

As described above, it was revealed that the bio-electrode, with the living body contact layer being formed by using the inventive bio-electrode composition, was excellent in electric conductivity, biocompatibility, and adhesion to an electro-conductive base material; excellent in holding the ionic material to prevent large lowering of electric conductivity even though it was wetted with water or dried; light-weight; and manufacturable at low cost.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A bio-electrode composition comprising a silsesquioxane bonded to an N-carbonyl sulfonamide salt, wherein the N-carbonyl sulfonamide salt is shown by the following general formula (1):

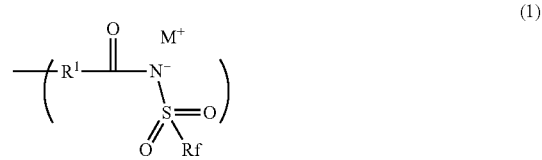

(1)

wherein $R^1$ represents a linear, branched, or cyclic alkylene group having 1 to 20 carbon atoms or an arylene group having 6 to 10 carbon atoms, with the alkylene group optionally having an aromatic group, an ether group, or an ester group; Rf represents a linear, branched, or cyclic alkyl group having 1 to 4 carbon atoms and containing at least one fluorine atom; M⁺ is an ion selected from a lithium ion, a sodium ion, a potassium ion, and a silver ion.

2. The bio-electrode composition according to claim 1, wherein the silsesquioxane bonded to an N-carbonyl sulfonamide salt has a repeating unit-a shown by the following general formula (2):

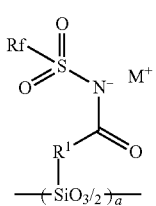

(2)

wherein R¹, Rf, and M⁺ are as defined above.

3. The bio-electrode composition according to claim 1, further comprising an adhesive resin as a component (B) in addition to the silsesquioxane bonded to an N-carbonyl sulfonamide salt as a component (A).

4. The bio-electrode composition according to claim 2, further comprising an adhesive resin as a component (B) in addition to the silsesquioxane bonded to an N-carbonyl sulfonamide salt as a component (A).

5. The bio-electrode composition according to claim 3, wherein the component (B) is one or more resins selected from a silicone resin, a (meth)acrylate resin, and a urethane resin.

6. The bio-electrode composition according to claim 4, wherein the component (B) is one or more resins selected from a silicone resin, a (meth)acrylate resin, and a urethane resin.

7. The bio-electrode composition according to claim 3, wherein the component (B) contains diorganosiloxane having an alkenyl group, and organohydrogenpolysiloxane having an SiH group.

8. The bio-electrode composition according to claim 5, wherein the component (B) contains diorganosiloxane having an alkenyl group, and organohydrogenpolysiloxane having an SiH group.

9. The bio-electrode composition according to claim 7, wherein the component (B) further contains a silicone resin having an $R_xSiO_{(4-x)/2}$ unit (wherein, R represents a substituted or unsubstituted monovalent hydrocarbon group having 1 to 10 carbon atoms, and "x" is a number in a range of 2.5 to 3.5) and an $SiO_2$ unit.

10. The bio-electrode composition according to claim 8, wherein the component (B) further contains a silicone resin having an $R_xSiO_{(4-x)/2}$ unit (wherein, R represents a substituted or unsubstituted monovalent hydrocarbon group having 1 to 10 carbon atoms, and "x" is a number in a range of 2.5 to 3.5) and an $SiO_2$ unit.

11. The bio-electrode composition according to claim 1, further comprising a carbon powder and/or a metal powder as a component (C).

12. The bio-electrode composition according to claim 11, wherein the carbon powder is either or both of carbon black and carbon nanotube.

13. The bio-electrode composition according to claim 11, wherein the metal powder is a powder of a metal selected from gold, silver, platinum, copper, tin, titanium, nickel, aluminum, tungsten, molybdenum, ruthenium, chromium, and indium.

14. The bio-electrode composition according to claim 1, further comprising an organic solvent as a component (D).

15. A bio-electrode comprising an electro-conductive base material and a living body contact layer formed on the electro-conductive base material;
wherein the living body contact layer is a cured material of the bio-electrode composition according to claim 1.

16. The bio-electrode according to claim 15, wherein the electro-conductive base material comprises one or more species selected from gold, silver, silver chloride, platinum, aluminum, magnesium, tin, tungsten, iron, copper, nickel, stainless steel, chromium, titanium, carbon, and an electro-conductive polymer.

17. A method for manufacturing a bio-electrode having an electro-conductive base material and a living body contact layer formed on the electro-conductive base material, comprising:
applying the bio-electrode composition according to claim 1 onto the electro-conductive base material; and
curing the bio-electrode composition; thereby forming the living body contact layer.

18. The method for manufacturing a bio-electrode according to claim 17, wherein the electro-conductive base material comprises one or more species selected from gold, silver, silver chloride, platinum, aluminum, magnesium, tin, tungsten, iron, copper, nickel, stainless steel, chromium, titanium, carbon, and an electro-conductive polymer.

19. An alkoxysilane compound shown by the following general formula (3):

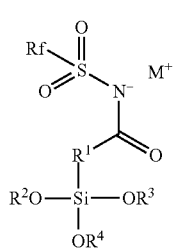

(3)

wherein R¹ represents a linear, branched, or cyclic alkylene group having 1 to 20 carbon atoms or an arylene group having 6 to 10 carbon atoms, with the alkylene group optionally having an aromatic group, an ether group, or an ester group; R² to R⁴ each represent a hydrogen atom or a linear or branched alkyl group having 1 to 4 carbon atoms; Rf represents a linear, branched, or cyclic alkyl group having 1 to 4 carbon atoms and containing at least one fluorine atom; M⁺ is an ion selected from a lithium ion, a sodium ion, a potassium ion, and a silver ion.

20. A silsesquioxane comprising a repeating unit shown by the following general formula (2), and having a weight average molecular weight in a range of 600 to 1000000,

(2)

wherein $R^1$ represents a linear, branched, or cyclic alkylene group having 1 to 20 carbon atoms or an arylene group having 6 to 10 carbon atoms, with the alkylene group optionally having an aromatic group, an ether group, or an ester group; Rf represents a linear, branched, or cyclic alkyl group having 1 to 4 carbon atoms and containing at least one fluorine atom; $M^+$ is an ion selected from a lithium ion, a sodium ion, a potassium ion, and a silver ion.

* * * * *